_(12)_ United States Patent
Divita et al.

US010118944B2

(10) Patent No.: US 10,118,944 B2
(45) Date of Patent: Nov. 6, 2018

(54) CELL PENETRATING PEPTIDES FOR INTRACELLULAR DELIVERY OF MOLECULES

(71) Applicant: AADIGEN, LLC, Pacific Palisades, CA (US)

(72) Inventors: Gilles Divita, Mauguio (FR); Sebastien Deshayes, Montpellier (FR); Karidia Konate, Montpellier (FR); May Catherine Morris, Mauguio (FR)

(73) Assignee: Aadigen LLC, Pacific Palisades, CA (US)

( * ) Notice: Subject to any disclaimer, the term of this patent is extended or adjusted under 35 U.S.C. 154(b) by 0 days.

(21) Appl. No.: 14/433,592

(22) PCT Filed: Oct. 4, 2013

(86) PCT No.: PCT/EP2013/070686
§ 371 (c)(1),
(2) Date: Apr. 3, 2015

(87) PCT Pub. No.: WO2014/053629
PCT Pub. Date: Apr. 10, 2014

(65) Prior Publication Data
US 2016/0145299 A1 May 26, 2016

(30) Foreign Application Priority Data

Oct. 4, 2012 (WO) .................. PCT/IB2012/055346

(51) Int. Cl.
| | |
|---|---|
| *C07K 7/06* | (2006.01) |
| *A61K 9/51* | (2006.01) |
| *A61K 47/48* | (2006.01) |
| *C07K 7/08* | (2006.01) |
| *A61K 47/60* | (2017.01) |
| *A61K 47/54* | (2017.01) |
| *A61K 47/62* | (2017.01) |
| *A61K 47/64* | (2017.01) |

(52) U.S. Cl.
CPC .............. *C07K 7/06* (2013.01); *A61K 9/5123* (2013.01); *A61K 47/542* (2017.08); *A61K 47/554* (2017.08); *A61K 47/60* (2017.08); *A61K 47/62* (2017.08); *A61K 47/64* (2017.08); *C07K 7/08* (2013.01); *A61K 9/5169* (2013.01)

(58) Field of Classification Search
None
See application file for complete search history.

(56) References Cited

U.S. PATENT DOCUMENTS

| 7,514,530 B2 | 4/2009 | Divita et al. |
| 9,376,468 B2 | 6/2016 | Divita et al. |
| 2014/0227344 A1 | 8/2014 | Divita et al. |
| 2016/0060296 A1 | 3/2016 | Divita et al. |
| 2016/0089447 A1 | 3/2016 | Divita et al. |
| 2016/0115199 A1 | 4/2016 | Divita et al. |

FOREIGN PATENT DOCUMENTS

| EP | 1 795 539 A1 | 6/2005 |
| WO | 2007/069090 A2 | 6/2007 |
| WO | WO-2007/069090 A2 | 6/2007 |
| WO | WO-2007/069090 A3 | 6/2007 |
| WO | WO-2008/036929 A2 | 3/2008 |
| WO | WO-2008/036929 A3 | 3/2008 |
| WO | WO-2011/153323 A2 | 12/2011 |
| WO | WO-2011/153323 A3 | 12/2011 |
| WO | WO-2012/137036 A1 | 10/2012 |
| WO | WO-2012/137150 A2 | 10/2012 |
| WO | WO-2012/137150 A3 | 10/2012 |
| WO | WO-2013/173307 A1 | 11/2013 |
| WO | WO-2014/053624 A1 | 4/2014 |

OTHER PUBLICATIONS

International Search Report issued in corresponding International Patent Application No. PCT/EP2013/070686 dated Dec. 11, 2013.
Kurzawa et al., "PEP and CADY-mediated delivery of fluorescent peptides and proteins into living cells," Biochimica et Biophysica Acta, 1798: 2274-2285 (2010).
Barre-Sinoussi, F. et al. (May 20, 1983). "Isolation of a T-Lymphotropic Retrovirus from a Patient at Risk for Acquired Immune Deficiency Syndrome (AIDS)," *Science* 220(4599):868-71.
Crombez, L. et al. (2009, e-pub. May 29, 2009). "Targeting Cyclin B1 Through Peptide-Based Delivery of siRNA Prevents Tumor Growth," *Nucleic Acid Research* 37(14):4559-4569.
Crombez, L. et al. (Jan. 2009, e-pub. Oct. 28, 2008). "A New Potent Secondary Amphipathic Cell-Penetrating Peptide for siRNA Delivery Into Mammalian Cells," *Mol. Ther.* 17(1):95-103.
Deshayes, S. et al. (2005). "Cell-penetrating Peptides: Tools for Intracellular Delivery of Therapeutics," *Cell Mol Life Sci.* 62:1839-1849.
Deshayes, S. et al. (2008, e-pub. Oct. 25, 2007). "Delivery of Proteins and Nucleic Acids Using a Non-Covalent Peptide-Based Strategy," *Adv. Drug Deliv. Rev.* 60:537-547.
Glover, D.J. et al. (Apr. 2005, e-pub. Mar. 10, 2005). "Towards Safe, Non-Viral Therapeutic Gene Expression in Humans," *Nat. Rev. Genet.* 6:299-310.
Gondeau, C. et al. (Apr. 8, 2005, e-pub. Jan. 11, 2005). "Design of a Novel Class of Peptide Inhibitors of Cyclin-Dependent Kinase/Cyclin Activation," *J.BioL Chem.* 280(14):13793-13800.
He, L. et al. (Jun. 28, 2007). "A MicroRNA Component of the p53 Tumour Suppressor Network," *Nature* 447(7148):1130-1134, 15 pages.

(Continued)

*Primary Examiner* — James H Alstrum-Acevedo
*Assistant Examiner* — Tara L Martinez
(74) *Attorney, Agent, or Firm* — Morrison & Foerster LLP

(57) ABSTRACT

A cell-penetrating peptide characterized in that it comprises an amino acid sequence consisting of a beta-alanine or a serine in N-terminal position, linked to a sequence consisting of 9 consecutive amino acids from the sequence RXWXRLWXRLR (SEQ ID NO:7), wherein X in position 2 is R or S and X in positions 4 and 8 are, independently from each other, W or F.

Figure 1:
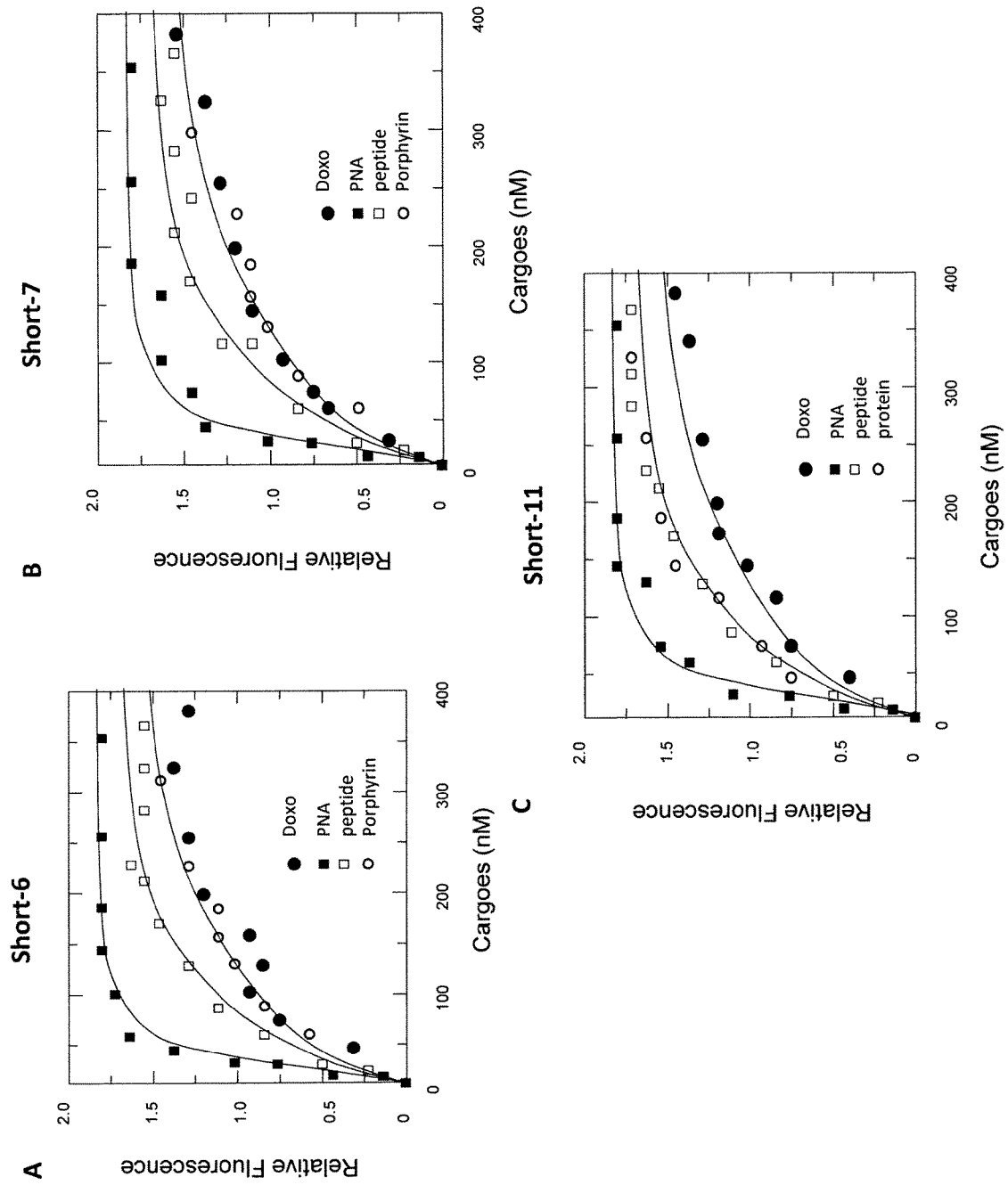

21 Claims, 6 Drawing Sheets
Specification includes a Sequence Listing.

(56) References Cited

OTHER PUBLICATIONS

Heitz, F. et al. (2009). "Themed Section: Vector Design and Drug Delivery Review. Twenty Years of Cell-Penetrating Peptides: From Molecular Mechanisms to Therapeutics," *British Journal of Pharmacology* 157:195-206.

Ji, Q. et al. (Aug. 28, 2009). MicroRNA miR-34 Inhibits Human Pancreatic Cancer Tumor-Initiating Cells, *PLoS One* 4(8):e6816, pp. 1-13.

Kim, Y-W. et al. (2011, e-pub. May 12, 2011). "Synthesis of All-Hydrocarbon Stapled α-Helical Peptides by Ring-Closing Olefin Methathesis," *Nature Protocols* 6(6):761-771.

Mery, J. et al. (Jul./Aug. 1992). "Disulfide Bond as Peptide-Resin Linkage in Boc-Bzl SPPS, for Potential Biochemical Applications," *Pept Res*. 5(4):233-40.

Morris, M.C. et al. (1997). "A New Peptide Vector for Efficient Delivery of Oligonucleotides Into Mammalian Cells," *Nucleic Acids Res*. 25(14):2730-2736.

Morris, M.C. et al. (Dec. 2001). "A Peptide Carrier for the Delivery of Biologically Active Proteins Into Mammalian Cells," *Nat. Biotechnol*. 19:1173-1176.

Morris et al. (2007, e-pub. Mar. 5, 2007) "A Non-Covalent Peptide-Based Carrier for in vivo Delivery of DNA Mimics," *Nucleic Acids Research* 35(7):e49.

Roisin, A. et al. (Mar. 5, 2004, e-pub. Dec. 10, 2003) "Inhibition of HIV-1 Replication by Cell-penetrating Peptides Binding Rev." *J. Biol. Chem*. 279(10):9208-14.

Thomas, A. et al. (2006, e-pub. Oct. 3, 2006). "Prediction of Peptide Structure: How Far are We?" *Proteins* 65:889-897.

Verdine, G.L. et al. (2012). "Stapled Peptides for Intracellular Drug Targets," Chapter 1 in *Methods in Enzymology*, 503:3-33.

Whitehead, K.A. et al. (Feb. 2009). "Knocking Down Barriers: Advances in siRNA Delivery," *Nat Rev Drug Discov*. 8:129-138.

Zhang, H. et al. (2011). "Antiviral Activity of α-Helical Stapled Peptides Designed from the HIV-1 Capsid Dimerization Domain," *Retrovirology* 8:28, pp. 1-18.

U.S. Appl. No. 15/160,939, filed May 20, 2016, by Divita et al.

SEQUENCE LISTING

```
<160> NUMBER OF SEQ ID NOS: 44

<210> SEQ ID NO 1
<211> LENGTH: 10
<212> TYPE: PRT
<213> ORGANISM: Artificial Sequence
<220> FEATURE:
<223> OTHER INFORMATION: synthesized peptide Short 6 VEPEP-31
<220> FEATURE:
<221> NAME/KEY: MISC_FEATURE
<222> LOCATION: (1)..(1)
<223> OTHER INFORMATION: Xaa = beta-Ala or Ser

<400> SEQUENCE: 1

Xaa Trp Trp Arg Leu Trp Trp Arg Leu Arg
1               5                   10
```

```
<210> SEQ ID NO 2
<211> LENGTH: 10
<212> TYPE: PRT
<213> ORGANISM: Artificial Sequence
<220> FEATURE:
<223> OTHER INFORMATION: synthesized peptide Short 7 VEPEP-31bis
<220> FEATURE:
<221> NAME/KEY: MISC_FEATURE
<222> LOCATION: (1)..(1)
<223> OTHER INFORMATION: Xaa = beta-Ala or Ser

<400> SEQUENCE: 2

Xaa Trp Phe Arg Leu Trp Phe Arg Leu Arg
1               5                   10

<210> SEQ ID NO 3
<211> LENGTH: 10
<212> TYPE: PRT
<213> ORGANISM: Artificial Sequence
<220> FEATURE:
<223> OTHER INFORMATION: synthesized peptide Short 8 VEPEP-31ter
<220> FEATURE:
<221> NAME/KEY: MISC_FEATURE
<222> LOCATION: (1)..(1)
<223> OTHER INFORMATION: Xaa = beta-Ala or Ser

<400> SEQUENCE: 3

Xaa Trp Phe Arg Leu Trp Trp Arg Leu Arg
1               5                   10

<210> SEQ ID NO 4
<211> LENGTH: 10
<212> TYPE: PRT
<213> ORGANISM: Artificial Sequence
<220> FEATURE:
<223> OTHER INFORMATION: synthesized peptide Short 9 VEPEP-31quater
<220> FEATURE:
<221> NAME/KEY: MISC_FEATURE
<222> LOCATION: (1)..(1)
<223> OTHER INFORMATION: Xaa = beta-Ala or Ser

<400> SEQUENCE: 4

Xaa Trp Trp Arg Leu Trp Phe Arg Leu Arg
1               5                   10

<210> SEQ ID NO 5
<211> LENGTH: 10
<212> TYPE: PRT
<213> ORGANISM: Artificial Sequence
<220> FEATURE:
<223> OTHER INFORMATION: synthesized peptide Short 10
<220> FEATURE:
<221> NAME/KEY: MISC_FEATURE
<222> LOCATION: (1)..(1)
<223> OTHER INFORMATION: Xaa = beta-Ala or Ser

<400> SEQUENCE: 5

Xaa Arg Trp Trp Arg Leu Trp Trp Arg Leu
1               5                   10

<210> SEQ ID NO 6
<211> LENGTH: 10
<212> TYPE: PRT
<213> ORGANISM: Artificial Sequence
<220> FEATURE:
<223> OTHER INFORMATION: synthesized peptide Short 11
<220> FEATURE:
<221> NAME/KEY: MISC_FEATURE
<222> LOCATION: (1)..(1)
```

```
<223> OTHER INFORMATION: Xaa = beta-Ala or Ser

<400> SEQUENCE: 6

Xaa Arg Ser Trp Phe Arg Leu Trp Phe Arg
1               5                   10

<210> SEQ ID NO 7
<211> LENGTH: 11
<212> TYPE: PRT
<213> ORGANISM: Artificial Sequence
<220> FEATURE:
<223> OTHER INFORMATION: synthesized peptide Group 3
<220> FEATURE:
<221> NAME/KEY: MISC_FEATURE
<222> LOCATION: (2)..(2)
<223> OTHER INFORMATION: Xaa = Arg or Ser
<220> FEATURE:
<221> NAME/KEY: MISC_FEATURE
<222> LOCATION: (4)..(4)
<223> OTHER INFORMATION: Xaa = Trp or Phe
<220> FEATURE:
<221> NAME/KEY: MISC_FEATURE
<222> LOCATION: (8)..(8)
<223> OTHER INFORMATION: Xaa = Trp or Phe

<400> SEQUENCE: 7

Arg Xaa Trp Xaa Arg Leu Trp Xaa Arg Leu Arg
1               5                   10

<210> SEQ ID NO 8
<211> LENGTH: 12
<212> TYPE: PRT
<213> ORGANISM: Artificial Sequence
<220> FEATURE:
<223> OTHER INFORMATION: synthesized peptide C4

<400> SEQUENCE: 8

Lys Lys Gln Val Arg Met Ala His Leu Val Leu Thr
1               5                   10

<210> SEQ ID NO 9
<211> LENGTH: 5
<212> TYPE: PRT
<213> ORGANISM: Artificial Sequence
<220> FEATURE:
<223> OTHER INFORMATION: synthesized peptide tetra

<400> SEQUENCE: 9

Gly Trp Ala Ser Cys
1               5

<210> SEQ ID NO 10
<211> LENGTH: 18
<212> TYPE: DNA
<213> ORGANISM: Artificial Sequence
<220> FEATURE:
<223> OTHER INFORMATION: synthesized oligonucleotide Cyc-Bct

<400> SEQUENCE: 10
tgccatcaag cttagagg                                                 18

<210> SEQ ID NO 11
<211> LENGTH: 16
<212> TYPE: PRT
<213> ORGANISM: Artificial Sequence
<220> FEATURE:
<223> OTHER INFORMATION: synthesized peptide VEPEP-3a
<220> FEATURE:
<221> NAME/KEY: MISC_FEATURE
```

```
<222> LOCATION: (1)..(1)
<223> OTHER INFORMATION: Xaa = acetylated residue
<220> FEATURE:
<221> NAME/KEY: MISC_FEATURE
<222> LOCATION: (1)..(1)
<223> OTHER INFORMATION: Xaa = beta-Ala or Ser
<220> FEATURE:
<221> NAME/KEY: MISC_FEATURE
<222> LOCATION: (16)..(16)
<223> OTHER INFORMATION: residue bound to a cysteamide

<400> SEQUENCE: 11

Xaa Lys Trp Phe Glu Arg Trp Phe Arg Glu Trp Pro Arg Lys Arg Arg
 1               5                  10                  15

<210> SEQ ID NO 12
<211> LENGTH: 16
<212> TYPE: PRT
<213> ORGANISM: Artificial Sequence
<220> FEATURE:
<223> OTHER INFORMATION: synthesized peptide VEPEP-3b
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Ala or Ser
<220> FEATURE:
<221> NAME/KEY: MISC_FEATURE
<222> LOCATION: (16)..(16)
<223> OTHER INFORMATION: residue bound to a cysteamide

<400> SEQUENCE: 12

Xaa Lys Trp Trp Glu Arg Trp Trp Arg Glu Trp Pro Arg Lys Arg Lys
 1               5                  10                  15

<210> SEQ ID NO 13
<211> LENGTH: 16
<212> TYPE: PRT
<213> ORGANISM: Artificial Sequence
<220> FEATURE:
<223> OTHER INFORMATION: synthesized peptide VEPEP-3c
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Ala or Ser
<220> FEATURE:
<221> NAME/KEY: MISC_FEATURE
<222> LOCATION: (16)..(16)
<223> OTHER INFORMATION: residue bound to a cysteamide

<400> SEQUENCE: 13

Xaa Arg Trp Trp Glu Lys Trp Trp Thr Arg Trp Pro Arg Lys Arg Lys
 1               5                  10                  15

<210> SEQ ID NO 14
<211> LENGTH: 16
<212> TYPE: PRT
<213> ORGANISM: Artificial Sequence
<220> FEATURE:
<223> OTHER INFORMATION: synthesized peptide VEPEP-3d
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
```

```
<222> LOCATION: (1)..(1)
<223> OTHER INFORMATION: Xaa = beta-Ala or Ser
<220> FEATURE:
<221> NAME/KEY: MISC_FEATURE
<222> LOCATION: (16)..(16)
<223> OTHER INFORMATION: residue bound to a cysteamide

<400> SEQUENCE: 14

Xaa Arg Trp Tyr Glu Lys Trp Tyr Thr Glu Phe Pro Arg Arg Arg
1               5                   10                  15

<210> SEQ ID NO 15
<211> LENGTH: 17
<212> TYPE: PRT
<213> ORGANISM: Artificial Sequence
<220> FEATURE:
<223> OTHER INFORMATION: synthesized peptide VEPEP-3e
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Ala or Ser
<220> FEATURE:
<221> NAME/KEY: MISC_FEATURE
<222> LOCATION: (17)..(17)
<223> OTHER INFORMATION: residue bound to a cysteamide

<400> SEQUENCE: 15

Xaa Arg Trp Trp Arg Leu Trp Trp Arg Ser Trp Phe Arg Leu Trp Arg
1               5                   10                  15

Arg

<210> SEQ ID NO 16
<211> LENGTH: 17
<212> TYPE: PRT
<213> ORGANISM: Artificial Sequence
<220> FEATURE:
<223> OTHER INFORMATION: synthesized peptide VEPEP-3f
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Ala or Ser
<220> FEATURE:
<221> NAME/KEY: MISC_FEATURE
<222> LOCATION: (17)..(17)
<223> OTHER INFORMATION: Xaa =  cysteamide

<400> SEQUENCE: 16

Xaa Leu Trp Trp Arg Arg Trp Trp Ser Arg Trp Trp Pro Arg Trp Arg
1               5                   10                  15

Arg

<210> SEQ ID NO 17
<211> LENGTH: 17
<212> TYPE: PRT
<213> ORGANISM: Artificial Sequence
<220> FEATURE:
<223> OTHER INFORMATION: synthesized peptide VEPEP-3g
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
```

```
<222> LOCATION: (1)..(1)
<223> OTHER INFORMATION: Xaa = beta-Ala or Ser
<220> FEATURE:
<221> NAME/KEY: MISC_FEATURE
<222> LOCATION: (17)..(17)
<223> OTHER INFORMATION: residue bound to a cysteamide

<400> SEQUENCE: 17

Xaa Leu Trp Trp Ser Arg Trp Trp Arg Ser Trp Phe Arg Leu Trp Phe
1               5                   10                  15
Arg

<210> SEQ ID NO 18
<211> LENGTH: 17
<212> TYPE: PRT
<213> ORGANISM: Artificial Sequence
<220> FEATURE:
<223> OTHER INFORMATION: synthesized peptide VEPEP-3h
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Ala or Ser
<220> FEATURE:
<221> NAME/KEY: MISC_FEATURE
<222> LOCATION: (17)..(17)
<223> OTHER INFORMATION: residue bound to a cysteamide

<400> SEQUENCE: 18

Xaa Lys Phe Trp Ser Arg Phe Trp Arg Ser Trp Phe Arg Leu Trp Arg
1               5                   10                  15
Arg

<210> SEQ ID NO 19
<211> LENGTH: 19
<212> TYPE: PRT
<213> ORGANISM: Artificial Sequence
<220> FEATURE:
<223> OTHER INFORMATION: synthesized peptide VEPEP-6a
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Ala or Ser
<220> FEATURE:
<221> NAME/KEY: MISC_FEATURE
<222> LOCATION: (19)..(19)
<223> OTHER INFORMATION: residue bound to a cysteamide

<400> SEQUENCE: 19

Xaa Leu Phe Arg Ala Leu Trp Arg Leu Leu Arg Ser Leu Trp Arg Leu
1               5                   10                  15
Leu Trp Lys

<210> SEQ ID NO 20
<211> LENGTH: 20
<212> TYPE: PRT
<213> ORGANISM: Artificial Sequence
<220> FEATURE:
<223> OTHER INFORMATION: synthesized peptide VEPEP-6b
<220> FEATURE:
<221> NAME/KEY: MISC_FEATURE
<222> LOCATION: (1)..(1)
<223> OTHER INFORMATION: acetylated residue
```

```
<220> FEATURE:
<221> NAME/KEY: MISC_FEATURE
<222> LOCATION: (1)..(1)
<223> OTHER INFORMATION: Xaa = beta-Ala or Ser
<220> FEATURE:
<221> NAME/KEY: MISC_FEATURE
<222> LOCATION: (20)..(20)
<223> OTHER INFORMATION: residue bound to a cysteamide

<400> SEQUENCE: 20

Xaa Leu Trp Arg Ala Leu Trp Arg Leu Trp Arg Ser Leu Trp Arg Leu
1               5                   10                  15

Leu Trp Lys Ala
            20

<210> SEQ ID NO 21
<211> LENGTH: 20
<212> TYPE: PRT
<213> ORGANISM: Artificial Sequence
<220> FEATURE:
<223> OTHER INFORMATION: synthesized peptide VEPEP-6c
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Ala or Ser
<220> FEATURE:
<221> NAME/KEY: MISC_FEATURE
<222> LOCATION: (20)..(20)
<223> OTHER INFORMATION: residue bound to a cysteamide

<400> SEQUENCE: 21

Xaa Leu Trp Arg Ala Leu Trp Arg Leu Leu Arg Ser Leu Trp Arg Leu
1               5                   10                  15

Trp Arg Lys Ala
            20

<210> SEQ ID NO 22
<211> LENGTH: 20
<212> TYPE: PRT
<213> ORGANISM: Artificial Sequence
<220> FEATURE:
<223> OTHER INFORMATION: synthesized peptide VEPEP-6d
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Ala or Ser
<220> FEATURE:
<221> NAME/KEY: MISC_FEATURE
<222> LOCATION: (20)..(20)
<223> OTHER INFORMATION: residue bound to a cysteamide

<400> SEQUENCE: 22

Xaa Leu Trp Arg Ala Leu Trp Arg Leu Trp Arg Ser Leu Trp Arg Leu
1               5                   10                  15

Trp Arg Lys Ala
            20

<210> SEQ ID NO 23
<211> LENGTH: 20
<212> TYPE: PRT
<213> ORGANISM: Artificial Sequence
<220> FEATURE:
```

-continued

```
<223> OTHER INFORMATION: synthesized peptide VEPEP-6e
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Ala or Ser
<220> FEATURE:
<221> NAME/KEY: MISC_FEATURE
<222> LOCATION: (20)..(20)
<223> OTHER INFORMATION: residue bound to a cysteamide

<400> SEQUENCE: 23

Xaa Leu Trp Arg Ala Leu Trp Arg Leu Leu Arg Ala Leu Trp Arg Leu
 1               5                  10                  15

Leu Trp Lys Ala
            20

<210> SEQ ID NO 24
<211> LENGTH: 20
<212> TYPE: PRT
<213> ORGANISM: Artificial Sequence
<220> FEATURE:
<223> OTHER INFORMATION: synthesized peptide VEPEP-6f
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Ala or Ser
<220> FEATURE:
<221> NAME/KEY: MISC_FEATURE
<222> LOCATION: (20)..(20)
<223> OTHER INFORMATION: residue bound to a cysteamide

<400> SEQUENCE: 24

Xaa Leu Trp Arg Ala Leu Trp Arg Leu Leu Arg Asn Leu Trp Arg Leu
 1               5                  10                  15

Leu Trp Lys Ala
            20

<210> SEQ ID NO 25
<211> LENGTH: 20
<212> TYPE: PRT
<213> ORGANISM: Artificial Sequence
<220> FEATURE:
<223> OTHER INFORMATION: synthesized peptide VEPEP-9a1
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Ala or Ser
<220> FEATURE:
<221> NAME/KEY: MISC_FEATURE
<222> LOCATION: (20)..(20)
<223> OTHER INFORMATION: residue bound to a cysteamide

<400> SEQUENCE: 25

Xaa Leu Arg Trp Trp Leu Arg Trp Ala Ser Arg Trp Phe Ser Arg Trp
 1               5                  10                  15

Ala Trp Trp Arg
            20
```

-continued

```
<210> SEQ ID NO 26
<211> LENGTH: 20
<212> TYPE: PRT
<213> ORGANISM: Artificial Sequence
<220> FEATURE:
<223> OTHER INFORMATION: synthesized peptide VEPEP-9a2
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Ala or Ser
<220> FEATURE:
<221> NAME/KEY: MISC_FEATURE
<222> LOCATION: (20)..(20)
<223> OTHER INFORMATION: residue bound to a cysteamide

<400> SEQUENCE: 26

Xaa Leu Arg Trp Trp Leu Arg Trp Ala Ser Arg Trp Ala Ser Arg Trp
1               5                   10                  15

Ala Trp Phe Arg
            20

<210> SEQ ID NO 27
<211> LENGTH: 19
<212> TYPE: PRT
<213> ORGANISM: Artificial Sequence
<220> FEATURE:
<223> OTHER INFORMATION: synthesized peptide VEPEP-9b1
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Ala or Ser
<220> FEATURE:
<221> NAME/KEY: MISC_FEATURE
<222> LOCATION: (19)..(19)
<223> OTHER INFORMATION: residue bound to a cysteamide

<400> SEQUENCE: 27

Xaa Arg Trp Trp Leu Arg Trp Ala Ser Arg Trp Ala Leu Ser Trp Arg
1               5                   10                  15

Trp Trp Arg

<210> SEQ ID NO 28
<211> LENGTH: 19
<212> TYPE: PRT
<213> ORGANISM: Artificial Sequence
<220> FEATURE:
<223> OTHER INFORMATION: synthesized peptide vVEPEP-9b2
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Ala or Ser
<220> FEATURE:
<221> NAME/KEY: MISC_FEATURE
<222> LOCATION: (19)..(19)
<223> OTHER INFORMATION: residue bound to a cysteamide

<400> SEQUENCE: 28

Xaa Arg Trp Trp Leu Arg Trp Ala Ser Arg Trp Phe Leu Ser Trp Arg
1               5                   10                  15
```

Trp Trp Arg

<210> SEQ ID NO 29
<211> LENGTH: 19
<212> TYPE: PRT
<213> ORGANISM: Artificial Sequence
<220> FEATURE:
<223> OTHER INFORMATION: synthesized peptide VEPEP-9c1
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Ala or Ser
<220> FEATURE:
<221> NAME/KEY: MISC_FEATURE
<222> LOCATION: (19)..(19)
<223> OTHER INFORMATION: residue bound to a cysteamide

<400> SEQUENCE: 29

Xaa Arg Trp Trp Leu Arg Trp Ala Pro Arg Trp Phe Pro Ser Trp Arg
1               5                   10                  15

Trp Trp Arg

<210> SEQ ID NO 30
<211> LENGTH: 19
<212> TYPE: PRT
<213> ORGANISM: Artificial Sequence
<220> FEATURE:
<223> OTHER INFORMATION: synthesized peptide VEPEP-9c2
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Ala or Ser
<220> FEATURE:
<221> NAME/KEY: MISC_FEATURE
<222> LOCATION: (19)..(19)
<223> OTHER INFORMATION: residue bound to a cysteamide

<400> SEQUENCE: 30

Xaa Arg Trp Trp Leu Arg Trp Ala Ser Arg Trp Ala Pro Ser Trp Arg
1               5                   10                  15

Trp Trp Arg

<210> SEQ ID NO 31
<211> LENGTH: 15
<212> TYPE: PRT
<213> ORGANISM: Artificial Sequence
<220> FEATURE:
<223> OTHER INFORMATION: synthesized peptide VEPEP-9d
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Ala or Ser
<220> FEATURE:
<221> NAME/KEY: MISC_FEATURE
<222> LOCATION: (15)..(15)
<223> OTHER INFORMATION: residue bound to a cysteamide

<400> SEQUENCE: 31

Xaa Trp Trp Arg Trp Trp Ala Ser Trp Ala Arg Ser Trp Trp Arg

-continued

```
<210> SEQ ID NO 32
<211> LENGTH: 15
<212> TYPE: PRT
<213> ORGANISM: Artificial Sequence
<220> FEATURE:
<223> OTHER INFORMATION: synthesized peptide VEPEP-9e
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Ala or Ser
<220> FEATURE:
<221> NAME/KEY: MISC_FEATURE
<222> LOCATION: (15)..(15)
<223> OTHER INFORMATION: residue bound to a cysteamide

<400> SEQUENCE: 32

Xaa Trp Trp Gly Ser Trp Ala Thr Pro Arg Arg Arg Trp Trp Arg
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: synthesized peptide VEPEP-9f
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Ala or Ser
<220> FEATURE:
<221> NAME/KEY: MISC_FEATURE
<222> LOCATION: (15)..(15)
<223> OTHER INFORMATION: residue bound to a cysteamide

<400> SEQUENCE: 33

Xaa Trp Trp Arg Trp Trp Ala Pro Trp Ala Arg Ser Trp Trp Arg
1               5                   10                  15

<210> SEQ ID NO 34
<211> LENGTH: 17
<212> TYPE: PRT
<213> ORGANISM: Artificial Sequence
<220> FEATURE:
<223> OTHER INFORMATION: synthesized peptide VEPEP-3bstapl
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Ala or Ser
<220> FEATURE:
<221> NAME/KEY: MISC_FEATURE
<222> LOCATION: (3)..(3)
<223> OTHER INFORMATION: Xaa =  Arg, which is linked to the Arg residue
      at position 10 by a hydrocarbon linkage
<220> FEATURE:
<221> NAME/KEY: MISC_FEATURE
<222> LOCATION: (10)..(10)
<223> OTHER INFORMATION: Xaa =  Arg, which is linked to the Arg residue
      at position 3 by a hydrocarbon linkage
<220> FEATURE:
<221> NAME/KEY: MISC_FEATURE
```

<222> LOCATION: (17)..(17)
<223> OTHER INFORMATION: residue bound to a cysteamide

<400> SEQUENCE: 34

Xaa Lys Xaa Trp Trp Glu Arg Trp Trp Xaa Ser Trp Pro Arg Lys Arg
1               5                   10                  15
Lys

<210> SEQ ID NO 35
<211> LENGTH: 17
<212> TYPE: PRT
<213> ORGANISM: Artificial Sequence
<220> FEATURE:
<223> OTHER INFORMATION: synthesized peptide VEPEP-3estap1
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Ala or Ser
<220> FEATURE:
<221> NAME/KEY: MISC_FEATURE
<222> LOCATION: (5)..(5)
<223> OTHER INFORMATION: Xaa = Arg, which is linked to the Ser residue
      at position 12 by a hydrocarbon linkage
<220> FEATURE:
<221> NAME/KEY: MISC_FEATURE
<222> LOCATION: (12)..(12)
<223> OTHER INFORMATION: Xaa = Ser, which is linked to the Arg residue
      at position 5 by a hydrocarbon linkage
<220> FEATURE:
<221> NAME/KEY: MISC_FEATURE
<222> LOCATION: (17)..(17)
<223> OTHER INFORMATION: residue bound to a cysteamide

<400> SEQUENCE: 35

Xaa Arg Trp Trp Xaa Leu Trp Trp Arg Ser Trp Xaa Arg Leu Trp Arg
1               5                   10                  15
Arg

<210> SEQ ID NO 36
<211> LENGTH: 19
<212> TYPE: PRT
<213> ORGANISM: Artificial Sequence
<220> FEATURE:
<223> OTHER INFORMATION: synthesized peptide ST-VEPEP-6a
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Ala or Ser
<220> FEATURE:
<221> NAME/KEY: MISC_FEATURE
<222> LOCATION: (8)..(8)
<223> OTHER INFORMATION: Xaa = Arg, which is linked to the Ser residue
      at position 12 by a hydrocarbon linkage
<220> FEATURE:
<221> NAME/KEY: MISC_FEATURE
<222> LOCATION: (12)..(12)
<223> OTHER INFORMATION: Xaa = Ser, which is linked to the Arg residue
      at position 8 by a hydrocarbon linkage
<220> FEATURE:
<221> NAME/KEY: MISC_FEATURE
<222> LOCATION: (19)..(19)
<223> OTHER INFORMATION: residue bound to a cysteamide

<400> SEQUENCE: 36

```
Xaa Leu Phe Arg Ala Leu Trp Xaa Leu Leu Arg Xaa Leu Trp Arg Leu
1               5                   10                  15

Leu Trp Lys

<210> SEQ ID NO 37
<211> LENGTH: 19
<212> TYPE: PRT
<213> ORGANISM: Artificial Sequence
<220> FEATURE:
<223> OTHER INFORMATION: synthesized peptide ST-VEPEP-6aa
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Ala or Ser
<220> FEATURE:
<221> NAME/KEY: MISC_FEATURE
<222> LOCATION: (8)..(8)
<223> OTHER INFORMATION: Xaa =  Arg, which is linked to the Ser residue
      at position 12 by a hydrocarbon linkage
<220> FEATURE:
<221> NAME/KEY: MISC_FEATURE
<222> LOCATION: (12)..(12)
<223> OTHER INFORMATION: Xaa =  Ser, which is linked to the Arg residue
      at position 8 by a hydrocarbon linkage
<220> FEATURE:
<221> NAME/KEY: MISC_FEATURE
<222> LOCATION: (19)..(19)
<223> OTHER INFORMATION: residue bound to a cysteamide

<400> SEQUENCE: 37

Xaa Leu Phe Leu Ala Arg Trp Xaa Leu Leu Arg Xaa Leu Trp Arg Leu
1               5                   10                  15

Leu Trp Lys

<210> SEQ ID NO 38
<211> LENGTH: 19
<212> TYPE: PRT
<213> ORGANISM: Artificial Sequence
<220> FEATURE:
<223> OTHER INFORMATION: synthesized peptide ST-VEPEP-6ab
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Ala or Ser
<220> FEATURE:
<221> NAME/KEY: MISC_FEATURE
<222> LOCATION: (8)..(8)
<223> OTHER INFORMATION: Xaa =  Ser, which is linked to the Ser residue
      at position 12 by a hydrocarbon linkage
<220> FEATURE:
<221> NAME/KEY: MISC_FEATURE
<222> LOCATION: (12)..(12)
<223> OTHER INFORMATION: Xaa =  Ser, which is linked to the Ser residue
      at position 8 by a hydrocarbon linkage
<220> FEATURE:
<221> NAME/KEY: MISC_FEATURE
<222> LOCATION: (19)..(19)
<223> OTHER INFORMATION: residue bound to a cysteamide

<400> SEQUENCE: 38

Xaa Leu Phe Arg Ala Leu Trp Xaa Leu Leu Arg Xaa Leu Trp Arg Leu
1               5                   10                  15

Leu Trp Lys
```

```
<210> SEQ ID NO 39
<211> LENGTH: 19
<212> TYPE: PRT
<213> ORGANISM: Artificial Sequence
<220> FEATURE:
<223> OTHER INFORMATION: synthesized peptide ST-VEPEP-6ad
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Ala or Ser
<220> FEATURE:
<221> NAME/KEY: MISC_FEATURE
<222> LOCATION: (8)..(8)
<223> OTHER INFORMATION: Xaa =  Ser, which is linked to the Ser residue
      at position 12 by a hydrocarbon linkage
<220> FEATURE:
<221> NAME/KEY: MISC_FEATURE
<222> LOCATION: (12)..(12)
<223> OTHER INFORMATION: Xaa =  Ser, which is linked to the Ser residue
      at position 8 by a hydrocarbon linkage
<220> FEATURE:
<221> NAME/KEY: MISC_FEATURE
<222> LOCATION: (19)..(19)
<223> OTHER INFORMATION: residue bound to a cysteamide

<400> SEQUENCE: 39

Xaa Leu Phe Leu Ala Arg Trp Xaa Leu Leu Arg Xaa Leu Trp Arg Leu
1               5                  10                  15

Leu Trp Lys

<210> SEQ ID NO 40
<211> LENGTH: 19
<212> TYPE: PRT
<213> ORGANISM: Artificial Sequence
<220> FEATURE:
<223> OTHER INFORMATION: synthesized peptide ST-VEPEP-6b
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Ala or Ser
<220> FEATURE:
<221> NAME/KEY: MISC_FEATURE
<222> LOCATION: (11)..(11)
<223> OTHER INFORMATION: Xaa =  Arg, which is linked to the Ser residue
      at position 15 by a hydrocarbon linkage
<220> FEATURE:
<221> NAME/KEY: MISC_FEATURE
<222> LOCATION: (15)..(15)
<223> OTHER INFORMATION: Xaa =  Ser, which is linked to the Arg residue
      at position 11 by a hydrocarbon linkage
<220> FEATURE:
<221> NAME/KEY: MISC_FEATURE
<222> LOCATION: (19)..(19)
<223> OTHER INFORMATION: residue bound to a cysteamide

<400> SEQUENCE: 40

Xaa Leu Phe Arg Ala Leu Trp Arg Leu Leu Xaa Ser Leu Trp Xaa Leu
1               5                  10                  15

Leu Trp Lys

<210> SEQ ID NO 41
<211> LENGTH: 19
<212> TYPE: PRT
<213> ORGANISM: Artificial Sequence
```

```
<220> FEATURE:
<223> OTHER INFORMATION: synthesized peptide ST-VEPEP-6ba
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Ala or Ser
<220> FEATURE:
<221> NAME/KEY: MISC_FEATURE
<222> LOCATION: (11)..(11)
<223> OTHER INFORMATION: Xaa =  Arg, which is linked to the Ser residue
     at position 15 by a hydrocarbon linkage
<220> FEATURE:
<221> NAME/KEY: MISC_FEATURE
<222> LOCATION: (15)..(15)
<223> OTHER INFORMATION: Xaa =  Ser, which is linked to the Arg residue
     at position 11 by a hydrocarbon linkage
<220> FEATURE:
<221> NAME/KEY: MISC_FEATURE
<222> LOCATION: (19)..(19)
<223> OTHER INFORMATION: residue bound to a cysteamide

<400> SEQUENCE: 41

Xaa Leu Phe Leu Ala Arg Trp Arg Leu Leu Xaa Ser Leu Trp Xaa Leu
1               5                   10                  15

Leu Trp Lys

<210> SEQ ID NO 42
<211> LENGTH: 19
<212> TYPE: PRT
<213> ORGANISM: Artificial Sequence
<220> FEATURE:
<223> OTHER INFORMATION: synthesized peptide ST-VEPEP-6bb
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Ala or Ser
<220> FEATURE:
<221> NAME/KEY: MISC_FEATURE
<222> LOCATION: (11)..(11)
<223> OTHER INFORMATION: Xaa =  Ser, which is linked to the Ser residue
     at position 15 by a hydrocarbon linkage
<220> FEATURE:
<221> NAME/KEY: MISC_FEATURE
<222> LOCATION: (15)..(15)
<223> OTHER INFORMATION: Xaa =  Ser, which is linked to the Ser residue
     at position 11 by a hydrocarbon linkage
<220> FEATURE:
<221> NAME/KEY: MISC_FEATURE
<222> LOCATION: (19)..(19)
<223> OTHER INFORMATION: residue bound to a cysteamide

<400> SEQUENCE: 42

Xaa Leu Phe Arg Ala Leu Trp Arg Leu Leu Xaa Ser Leu Trp Xaa Leu
1               5                   10                  15

Leu Trp Lys

<210> SEQ ID NO 43
<211> LENGTH: 19
<212> TYPE: PRT
<213> ORGANISM: Artificial Sequence
<220> FEATURE:
<223> OTHER INFORMATION: synthesized peptide ST-VEPEP-6bd
<220> FEATURE:
<221> NAME/KEY: MISC_FEATURE
<222> LOCATION: (1)..(1)
```

```
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Ala or Ser
<220> FEATURE:
<221> NAME/KEY: MISC_FEATURE
<222> LOCATION: (11)..(11)
<223> OTHER INFORMATION: Xaa = Ser, which is linked to the Ser residue
      at position 15 by a hydrocarbon linkage
<220> FEATURE:
<221> NAME/KEY: MISC_FEATURE
<222> LOCATION: (15)..(15)
<223> OTHER INFORMATION: Xaa = Ser, which is linked to the Ser residue
      at position 11 by a hydrocarbon linkage
<220> FEATURE:
<221> NAME/KEY: MISC_FEATURE
<222> LOCATION: (19)..(19)
<223> OTHER INFORMATION: residue bound to a cysteamide

<400> SEQUENCE: 43

Xaa Leu Phe Leu Ala Arg Trp Arg Leu Leu Xaa Ser Leu Trp Xaa Leu
1               5                   10                  15

Leu Trp Lys

<210> SEQ ID NO 44
<211> LENGTH: 19
<212> TYPE: PRT
<213> ORGANISM: Artificial Sequence
<220> FEATURE:
<223> OTHER INFORMATION: synthesized peptide ST-VEPEP-6c
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Ala or Ser
<220> FEATURE:
<221> NAME/KEY: MISC_FEATURE
<222> LOCATION: (5)..(5)
<223> OTHER INFORMATION: Xaa = Arg, which is linked to the Ser residue
      at position 12 by a hydrocarbon linkage
<220> FEATURE:
<221> NAME/KEY: MISC_FEATURE
<222> LOCATION: (12)..(12)
<223> OTHER INFORMATION: Xaa = Ser, which is linked to the Arg residue
      at position 5 by a hydrocarbon linkage
<220> FEATURE:
<221> NAME/KEY: MISC_FEATURE
<222> LOCATION: (19)..(19)
<223> OTHER INFORMATION: residue bound to a cysteamide

<400> SEQUENCE: 44

Xaa Leu Phe Ala Xaa Leu Trp Arg Leu Leu Arg Xaa Leu Trp Arg Leu
1               5                   10                  15

Leu Trp Lys
```

CELL PENETRATING PEPTIDES FOR INTRACELLULAR DELIVERY OF MOLECULES

CROSS REFERENCE TO RELATED APPLICATIONS

This application is the National Stage filing of PCT/EP2013/070686, entitled "CELL PENETRATING PEPTIDES FOR INTRACELLULAR DELIVERY OF MOLECULES" with the International Filing Date of Oct. 4, 2013, which claims the benefit of priority from PCT/IB2012/055346, filed on Oct. 4, 2012, each of which is hereby incorporated by reference in its entirety for all purposes as if put forth in full below.

The content of the following submission on ASCII text file is incorporated herein by reference in its entirety: a computer readable form (CRF) of the Sequence Listing (file name: 737372000700SubSeqList2.txt, date recorded: Jun. 20, 2017, size: 24 KB).

The present invention pertains to the field of intracellular delivery of molecules such as nucleic acids and small hydrophobic molecules. In particular, the invention relates to a new cell-penetrating peptide (CPP) family, which exhibits a high efficacy and a low toxicity.

Although small molecules remain the major drugs used in clinic, in numerous cases, their therapeutic impact has reached limitations such as insufficient capability to reach targets, lack of specificity, requirement for high doses leading to toxicity and major side effects. Over the past ten years, in order to circumvent limitations of small molecules and of gene-based therapies, we have witnessed a dramatic acceleration in the discovery of larger therapeutic molecules such as proteins, peptides and nucleic acids which present a high specificity for their target but do not follow Lipinski's rules. Pharmaceutical potency of these molecules remains restricted by their poor stability in vivo and by their low uptake in cells. Therefore, "delivery" has become a central piece of the therapeutic puzzle and new milestones have been established to validate delivery strategies: (a) lack of toxicity, (b) efficiency at low doses in vivo. (c) easy to handle for therapeutic applications (d) rapid endosomal release and (e) ability to reach the target. Although viral delivery strategies had given much hope for gene and cellular therapies, their clinical application has suffered from side- and toxicity-effects [1,2]. Researches were mainly focused on the development of non-viral strategies, and different methods have been proposed including lipid, polycationic nanoparticles and peptide-based formulations, but only few of these technologies have been efficient in vivo and have reached the clinic. Cell Penetrating Peptides (CPP) are one of the most promising non-viral strategies. Although definition of CPPs is constantly evolving, they are generally described as short peptides of less than 30 amino acids either derived from proteins or from chimeric sequences. They are usually amphipathic and possess a net positive charge [3-5]. CPPs are able to penetrate biological membranes, to trigger the movement of various biomolecules across cell membranes into the cytoplasm and to improve their intracellular routing, thereby facilitating interactions with the target. CPPs can be subdivided into two main classes, the first requiring chemical linkage with the cargo and the second involving the formation of stable, non-covalent complexes. CPPs from both strategies have been reported to favour the delivery of a large panel of cargos (plasmid DNA, oligonucleotide, siRNA, PNA, protein, peptide, liposome, nanoparticle . . . ) into a wide variety of cell types and in vivo models [3-7].

Twenty years ago, the concept of protein transduction domain (PTD) was proposed based on the observation that some proteins, mainly transcription factors, could shuttle within cells and from one cell to another [for review see ref 3,4]. The first observation was made in 1988, by Frankel and Pabo. They showed that the transcription-transactivating (Tat) protein of HIV-1 could enter cells and translocate into the nucleus. In 1991, the group of Prochiantz reached the same conclusions with the *Drosophila* Antennapedia homeodomain and demonstrated that this domain was internalized by neuronal cells. These works were at the origin of the discovery in 1994 of the first Protein Transduction Domain: a 16 mer-peptide derived from the third helix of the homeodomain of Antennapedia named Penetratin. In 1997, the group of Lebleu identified the minimal sequence of Tat required for cellular uptake and the first proofs-of-concept of the application of PTD in vivo, were reported by the group of Dowdy, for the delivery of small peptides and large proteins. Historically, the notion of Cell Penetrating Peptide (CPP) was introduced by the group of Langel, in 1998, with the design of the first chimeric peptide carrier, the Transportan, which derived from the N-terminal fragment of the neuropeptide galanin, linked to mastoparan, a wasp venom peptide. Transportan has been originally reported to improve the delivery of PNAs both in cultured cells and in vivo. In 1997, the group of Heitz and Divita proposed a new strategy involving CPP in the formation of stable but non-covalent complexes with their cargo [7]. The strategy was first based on the short peptide carrier (MPG) consisting of two domains: a hydrophilic (polar) domain and a hydrophobic (apolar) domain. MPG was designed for the delivery of nucleic acids [7]. The primary amphipathic peptide Pep-1 was then proposed for non-covalent delivery of proteins and peptides [8]. Then the groups of Wender and of Futaki demonstrated that polyarginine sequences (Arg8) are sufficient to drive small and large molecules into cells and in vivo. Ever since, many CPPs derived from natural or unnatural sequences have been identified and the list is constantly increasing. Peptides have been derived from VP22 protein of Herpes Simplex Virus, from calcitonin, from antimicrobial or toxin peptides, from proteins involved in cell cycle regulation, as well as from polyproline-rich peptides [reviews 4-6].

The inventors have now designed a new family of 10 amino acid cell-penetrating peptides for the delivery of peptides/proteins and hydrophobic molecules, named VEPEP-5. Delivery strategies using VEPEP-5 peptides as the outer layer of nanoparticles are referred to as NANOPEP-5.

VEPEP-5 are short primary and, in certain cases, secondary amphipathic 10 amino acid peptides forming stable nanoparticles with molecules such as peptides, peptide-analogues, PNAs and small hydrophobic molecules, hereafter designated as "SHM" VEPEP-5 vectors comprise or consist of an amino acid sequence consisting of a beta-alanine or a serine in N-terminal position, linked to a sequence consisting of 9 consecutive amino acids from the sequence

RXWXRLWXRLR,                    (SEQ ID NO: 7)

wherein:
X in position 2 is R or S; and
X in positions 4 and 8 are, independently from each other, W or F.

Non-limitative examples of VEPEP-5 peptides according to the present invention comprise an amino acid sequence selected from the group consisting of:

X₁WWRLWWRLR                     (SEQ ID No: 1)

X₁WFRLWFRLR                     (SEQ ID No: 2)

X₁WFRLWWRLR,                    (SEQ ID No: 3)

X₁WWRLWFRLR,                    (SEQ ID No: 4)

X₁RWWRLWWRL,                    (SEQ ID No: 5)
and

X₁RSWFRLWFR,                    (SEQ ID No: 6)

wherein X₁ is beta-A or S.

The present invention also pertains to a stapled cell-penetrating peptide derived from a VEPEP-5 cell-penetrating peptide as described above. A "stapled" peptide designates a peptide which comprises a chemical linkage (in addition to the amino acid chain) between two residues. In a particular embodiment of stapled VEPEP-5 peptides, the VEPEP-5 peptide comprises a hydrocarbon linkage between two residues which are separated by three or six residues. The skilled artisan can obtain these peptides by using techniques which are available in the art, for example as described by Verdine and Hilinski, Methods in Enzymology, 2012 [12].

VEPEP-5 strategy improves both ex-vivo and in vivo delivery and efficiency of peptide/protein/peptide analogue and small hydrophobic molecules, without activating the innate immune response or inducing toxic side effects.

According to a preferred embodiment, a cell-penetrating peptide of the present invention further comprises, covalently linked to the N-terminal end of the amino acid sequence, one or several chemical entities selected in the group consisting of an acetyl, a fatty acid, a cholesterol, a poly-ethylene glycol, a nuclear localization signal, a nuclear export signal, an antibody, a polysaccharide and a targeting molecule (peptide, fatty acid, saccharide).

In particular, PEGylation of VEPEP-5 peptide is advantageous for stabilizing nanoparticles in vivo.

In addition or alternatively, a cell-penetrating peptide according to the invention can comprise, covalently linked to the C-terminal end of its amino acid sequence, one or several groups selected in the group consisting of a cysteamide, a cysteine, a thiol, an amide, a nitrilotriacetic acid optionally substituted, a carboxyl, a linear or ramified C1-C6 alkyl optionally substituted, a primary or secondary amine, an osidic derivative, a lipid, a phospholipid, a fatty acid, a cholesterol, a poly-ethylene glycol, a nuclear localization signal, nuclear export signal, an antibody, a polysaccharide and a targeting molecule.

Another aspect of the present invention is a complex comprising a cell-penetrating peptide as described above and a cargo selected amongst protein/peptide and hydrophobic molecules. Examples of polypeptide cargoes are proteins of at most 15 kDa, such as nanobodies, small peptides, cyclic peptides, peptide-based biomarkers, bio-drugs, PNAs or oligonucleotides. In a preferred embodiment of the complex according to the invention, the cargo is a small molecule (size lower than 1.5 kDa), either hydrophobic or charged. Preferred cargos in the complexes according to the present invention are anticancer and antiviral drugs, as well as cosmetic agents. Non-limitative examples of small hydrophobic molecules which can be used include amino acids, di- or tri-peptides (labelled or not) daunomycin, Paclitaxel, doxorubicin, AZT, porphyrin, fluorescently labelled-nucleosides or nucleotides (FAM-Guanosine, CY5_UTP, CY3-UTP), hydrophobic maghemite (contrast agents or magnetic nanoparticles $Fe_2O_3$) and fluorescent dyes.

The size of the complexes described above is preferably between 50 and 200 nm (the size of the complex herein designates its mean diameter).

In the complexes according to the invention, the cargo/VEPEP-5 molar ratio depends on the nature and size of the cargo, but is generally comprised between 1/1 and 1/50. For small peptide cargoes, the cargo/VEPEP-5 molar ratio preferably ranges from 1/5 to 1/20. For small molecule cargoes, the cargo/VEPEP-5 molar ratio preferably ranges from 1/3 to 1/10. For protein cargoes, the cargo/VEPEP-5 molar ratio preferably ranges from 1/10 to 1/20

According to an advantageous embodiment of the complexes as described above, the VEPEP-5 peptides comprise a polyethylene glycol group or an acetyl group covalently linked to their N-terminus, and/or a cysteamide group covalently linked to their C-terminus.

The above complexes can be advantageously used as "core shells" for obtaining bigger complexes, or nanoparticles, by an additional step of coating the cargo/VEPEP-5 complex with another layer of cell-penetrating peptides, which can be identical to or different from the VEPEP-5 peptides described above. Examples of such nanoparticles are VEPEP-5/CADY (wherein CADY is a CPP as described in EP1795539 and in [11]), VEPEP-5/PEP-1 (wherein Pep-1 is a CPP as described in [8]), VEPEP-5/MPG (wherein MPG is a CPP as described in U.S. Pat. No. 7,514,530 and in [7, 10]), as well as nanoparticles with an outer layer made of a CPP belonging to another VEPEP family, for example selected from the following list:

VEPEP-3a:
                                (SEQ ID No: 11)
Ac-X₁KWFERWFREWPRKRR-cysteamide VEPEP-3b:
                                (SEQ ID No: 12)
Ac-X₁KWWERWWREWPRKRK-cysteamide VEPEP-3c:
                                (SEQ ID No: 13)
Ac-X₁RWWEKWWTRWPRKRK-cysteamide, VEPEP-3d:
                                (SEQ ID No 14)
Ac-X₁RWYEKWYTEFPRRRR-cysteamide, VEPEP-3e:
                                (SEQ ID No: 15)
Ac-X₁RWWRLWWRSWFRLWRR-cysteamide -continued VEPEP-3f:
(SEQ ID No: 16)
Ac-X₁LWWRRWWSRWWPRWRR-cysteamide VEPEP-3g:
(SEQ ID No: 17)
Ac-X₁LWWSRWWRSWFRLWFR-cysteamide, VEPEP-3h:
(SEQ ID No: 18)
Ac-X₁KFWSRFWRSWFRLWRR-cysteamide, VEPEP-6a:
(SEQ ID No: 19)
Ac-X₁LFRALWRLLRSLWRLLWK-cysteamide VEPEP-6b:
(SEQ ID No: 20)
Ac-X₁LWRALWRLWRSLWRLLWKA-cysteamide VEPEP-6c:
(SEQ ID No: 21)
Ac-X₁LWRALWRLLRSLWRLWRKA-cysteamide VEPEP-6d:
(SEQ ID No: 22)
Ac-X₁LWRALWRLWRSLWRLWRKA-cysteamide VEPEP-6e:
(SEQ ID No: 23)
Ac-X₁LWRALWRLLRALWRLLWKA-cysteamide VEPEP-6f:
(SEQ ID No: 24)
Ac-X₁LWRALWRLLRNLWRLLWKA-cysteamide VEPEP-9a1:
(SEQ ID No: 25)
Ac-X₁LRWWLRWASRWFSRWAWWR-cysteamide VEPEP-9a2:
(SEQ ID No: 26)
Ac-X₁LRWWLRWASRWASRWAWFR-cysteamide VEPEP-9b1:
(SEQ ID No: 27)
Ac-X₁RWWLRWASRWALSWRWWR-cysteamide VEPEP-9b2:
(SEQ ID No: 28)
Ac-X₁RWWLRWASRWFLSWRWWR-cysteamide VEPEP-9c1:
(SEQ ID No: 29)
Ac-X₁RWWLRWAPRWFPSWRWWR-cysteamide VEPEP-9c2:
(SEQ ID No: 30)
Ac-X₁RWWLRWASRWAPSWRWWR-cysteamide VEPEP-9d:
(SEQ ID No: 31)
Ac-X₁WWRWWASWARSWWR-cysteamide VEPEP-9e:
(SEQ ID No: 32)
Ac-X₁WWGSWATPRRRWWR-cysteamide VEPEP-9f:
(SEQ ID No: 33)
Ac-X₁WWRWWAPWARSWWR-cysteamide VEPEP-3bstapl:
(SEQ ID No: 34)
Ac-X₁KR$_S$WWERWWR$_S$SWPRKRK-cysteamide VEPEP-3estapl:
(SEQ ID No: 35)
Ac-X₁RWWR$_S$LWWRSWS$_S$RLWRR-cysteamide -continued ST-VEPEP-6a:
(SEQ ID No: 36)
Ac-X₁LFRALWR$_S$LLRS$_S$LWRLLWK-cysteamide ST-VEPEP-6aa:
(SEQ ID No: 37)
Ac-X₁LFLARWR$_S$LLRS$_S$LWRLLWK-cysteamide ST-VEPEP-6ab:
(SEQ ID No: 38)
Ac-X₁LFRALWS$_S$LLRS$_S$LWRLLWK-cysteamide ST-VEPEP-6ad:
(SEQ ID No: 39)
Ac-X₁LFLARWS$_S$LLRS$_S$LWRLLWK-cysteamide ST-VEPEP-6b:
(SEQ ID No: 40)
Ac-X₁LFRALWRLLR$_S$SLWS$_S$LLWK-cysteamide ST-VEPEP-6ba:
(SEQ ID No: 41)
Ac-X₁LFLARWRLLR$_S$SLWS$_S$LEWK-cysteamide ST-VEPEP-6bb:
(SEQ ID No: 42)
Ac-X₁LFRALWRELS$_S$SLWS$_S$LLWK-cysteamide ST-VEPEP-6bd:
(SEQ ID No: 43)
Ac-X₁LFLARWRLLS$_S$SLWS$_S$LLWK-cysteamide ST-VEPEP-6c:
(SEQ ID No: 44)
Ac-X₁LFAR$_S$LWRLLRS$_S$LWRLLWK-cysteamide, as well as variants thereof (regarding the amino acid sequence and/or the N- and C-terminal chemical groups), wherein $X_1$ is beta-A or S and wherein the residues followed by an inferior "s" are linked by a hydrocarbon linkage. Preferred variants of the above sequences for forming nanoparticles according to the invention are PEGylated at their N-terminal extremity instead of being acetylated.

Another aspect of the present invention pertains to nanoparticles made of a "core shell" comprising a cargo and a first carrier molecule, surrounded by VEPEP-5 peptides. These are herein referred to as "NANOPEP-5" particles. NANOPEP-5 technology constitutes a "custom-built" delivery system containing a common core particle, trapping therapeutic molecule, with surface VEPEP-5 peptides which are preferably functionalized for tumour or tissue targeting in viva. From a structural point of view, NANOPEP-5 particles are constituted by a "core" which is coated by a layer of VEPEP-5 peptides. The "core" corresponds to a complex comprising a cargo and a vector or carrier such as a first cell-penetrating peptide, a liposome, a polycationic structure, a carbon nanoparticle, etc. In NANOPEP-5 particles, the layer of VEPEP-5 peptides (peripheral peptide) stabilizes the particle and can be functionalized. Functionalizing NANOPEP-5 particle surface with either cholesterol, lipid, PEG-molecules improves particles stability in viva, favours their administration by either systemic or topical route and allows rapid liberation of active cargoes within tumor cells or tissues. Functionalization of the surface of NANOPEP-5 particles with small FAB fragments, peptides, antibodies and lipids has been shown to favour in viva tissue or tumor targeting. Also, Functionalizing NANOPEP-5 particle surface with polysaccharide such as PLGA, can be used as formulation for slow release of drug and cargo and allow a long term response in viva. N-terminal PEGylation of at least part of the VEPEP-5 peptides surrounding the NANOPEP-5 particles increases the biodistribution of cargoes in the tumour, probably by stabilizing the NANOPEP-5 particles in the plasma.

NANOPEP-5 technology improves both cellular and in viva delivery of biologically active cargoes and has been validated on a large set of cell lines including adherent and suspension cell lines, hard to transfect cell lines. NANOPEP-5 particles strongly interact with cell membranes and enter the cell independently of the endosomal pathway or rapidly escape from early endosomes. NANOPEP-5 technology presents several advantages including rapid delivery with very high efficiency, stability in physiological buffers, protection of the cargo against degradation, lack of toxicity and of sensitivity to serum, ability of forming mix nanoparticles, can be functionalized can be applied to the delivery of different types of cargoes into a large variety of cell lines as well as in animal models, thereby constituting powerful tools for basic research and therapeutic applications. NANOPEP-5 technology can be applied both at therapeutic and diagnostic/theragnostic levels, as well as for imaging.

In a particular embodiment of NANOPEP-5 particles according to the present invention, the cargo is complexed to a first cell-penetrating peptide, which can be, for example, selected amongst CADY, MPG, PEP-1, PPTG1, poly Arginine motif, VEPEP-family peptide (VEPEP-3, VEPEP-5, VEPEP-6, VEPEP-9, stapled or not) as described above (such as SEQ ID Nos: 1 to 7 and 11 to 44 and variants thereof), or any other known CPP. This cargo/CPP complex is then coated with a layer of VEPEP-5 peptides. According to this embodiment, the skilled artisan will advantageously choose the first CPP depending on the nature of the cargo, so that the complex of cargo and first CPP is stable. Hence, a wide diversity of cargoes can be included in NANOPEP-5 particles.

In the nanoparticles as above-described, the core/VEPEP-5 molar ratio depends on the nature and size of the core, but is generally comprised between 1/1 and 1/50. For small peptide/CPP cores, the core/peripheral VEPEP-5 molar ratio preferably ranges from 1/5 to 1/30, depending on the nature of peptide cargo (hydrophobicity and charge).

In a preferred embodiment of the nanoparticles according to the invention, the size of the nanoparticle is between 20 and 300 nm.

According to an advantageous embodiment of the NANOPEP-5 particles according to the invention, the VEPEP-5 peptides forming the peripheral layer of the nanoparticles comprise a poly-ethylene glycol or an acetyl group covalently linked to their N-terminus, and/or a cysteamide group covalently linked to their C-terminus.

According to another preferred embodiment, the core shell of the particles is coated with a VEPEP-5 peptide functionalized with NTA (for example, a VEPEP-5 peptide with nitrilotriacetic acid covalently linked to its C-terminus). This allows the subsequent attachment to the surface of the particle, of any protein (or other molecule) harboring a histidine tag. This strategy offers the major advantage of having a common two-layers particles "NANOPEPHIS-5" which can be associated to any His-tagged molecule.

In particular embodiments of the complexes and nanoparticles according to the invention, at least part of the VEPEP-5 cell-penetrating peptides are bound to a targeting molecule. In the case of NANOPEP-5 particles, at least part of the cell-penetrating peptides which are at the periphery of the nanoparticle are preferentially bound to a targeting molecule. Examples of targeting molecules include antibodies, nanobodies and Fc or FAB fragments (for example targeting HEK2/MUC1/EGF/XCCR4), ligands, especially targeting receptors which are over-expressed at the surface of certain cell-types and homing peptides specific of selected organs. Non-limitative examples of such ligands and homing peptides are: RGD-peptide, horning targeting peptides (brain NT1 peptide, Ganglion GM1 peptide, as well as all other previously described peptides for tissues and cell line targeting), folic acid, polysaccharides, and matrix metalloprotease targeting peptide motif (MMP-9 or MMP3 for tumour selectivity).

According to a particular embodiment of the present invention, the complexes or nanoparticles are formulated se that they can be stored during several months without losing their stability and functional efficacy. In particular, the complexes and nanoparticles of the invention can advantageously be lyophilized in the presence of a sugar. Non-limitative examples of sugars which can be used to that aim are sucrose, glucose, manitol and a mix thereof, and they can be used, for example, in a concentration ranging from 5% to 20%, preferably 5% to 10%, it being understood that a concentration of 5% is obtained by adding 5 grams per litre of solution before lyophilization.

Another aspect of the present invention is the use of a complex or nanoparticle as above-described, as a medicament and as a marker or an imaging agent.

The present invention also pertains to a therapeutic, cosmetic or diagnostic composition comprising a complex or a nanoparticle as described above. For example, a composition comprising a complex or nanoparticle having a peptide targeting protein/protein interactions, involving essential protein CDK and Cyclin required for cell cycle progression as a cargo, and a targeting molecule specific for tumour cells (for example: RGD-peptide, folic acid, MUC-1 or HEK2 antibodies or nanobodies), is part of the present invention. Depending on the application, this composition can be formulated for intravenous, intratumoral, topical, intrarectal, intranasal, transdermal, or intradermal administration, or for administration via a mouth spray, or for administration as a subcutaneous implant for slow release of a drug.

The present invention also pertains to a method for delivering a molecule into a cell in vitro, comprising a step of putting said cell into contact with a complex or nanoparticle as described above.

One of the major advantages of using short peptides with a size of 10 and less residues is the lack of innate immune response associated thereto. Short peptides do not induce allergic response and therefore can be administered by trans-dermal route and topically without any risk of inflammatory response, in contrast to longer peptides. Moreover, the risk of immune response following intravenous injection of VEPEP-5 is negligible.

Several aspects of the present invention are further developed in the following examples, illustrated by the figures (which are described in the examples).

EXAMPLE 1

Materials and Methods

VEPEP-5 Peptides

All peptides were synthesized by solid-phase peptide synthesis using AEDI-expensin resin with (fluorenylmethoxy)-carbonyl (Fmoc) on a Pioneer Peptide Synthesizer (Pioneer™, Applied Biosystems, Foster City, Calif.) starting from Fmoc-PAL-PEG-PS resin at a 0.2 mmol scale. The coupling reactions were performed with 0.5 M of HATU in the presence of 1 M of DIEA. Protecting group removal and final cleavage from the resin were carried out with TFA/Phenol/$H_2O$/Thioanisol/Ethanedithiol (82.5/5/5/5/2.5%) for 3 h 30 min. All the peptides presented a cysteamide group at the C-terminus and were acetylated at the N-terminus. The peptide synthesis started by the C-terminus, using an AEDI-expensin resin starting with a cysteamide link, as described by Mery et al, 1992. All the peptides contained a beta-Alanine or a serine at the N-terminus to favour any further functionalization without using the C-terminal cysteamide group.

Functionalization of Vepep-5

Two approaches were used for peptide functionalization (1) Peptide conjugations with peptide, antibody, pegylation, NTA, cholesterol, stearylation, were performed at the primary amino group of the N-terminal residue, through a beta alanine or serine. It is advantageous to maintain the C-terminal cysteamide free, since it is known to be required to stabilize the particle through disulfide bonds (SH—SH). Functionalized peptides were further purified by Reverse Phase-HPLC and analyzed by electro-spray ionization mass spectroscopy.

(2) Peptide conjugations were also performed via disulfide bound using the SH-group of the cysteamide moiety of the peptide.

X: Cholesterol, Pegylation, stearyl, palmitoyl, small FC or FAB fragments, nanobody, nitrilotriacetic acid (2×NTA), tissues targeting peptides (brain, lung, lymph node, pancreas . . . ).

VEPEP-5 Structure

VEPEP-5 peptides are tryptophan rich peptides; they are highly versatile and show a strong structural polymorphism. VEPEP-5 are unfolded in solution in free form as well as in the presence of lipid or artificial cellular membranes or of cargos such as peptide or small molecules.

Peptides & Proteins

Peptide targeting CDK/Cyclin (C4: KKQVRMAHLVLT (SEQ ID No: 8))

was obtained for Polypeptide. Fluorescently labelled (Cy5 and Cy3) tetra ((GWASC-dye (SEQ ID No: 9))

peptides were also ex obtained for Polypeptide. Proteins; His-tagged-GFP was overexpressed in *E. coli*.

PNA

Short oligonucleotides PNA and 5' Alexa$^{700}$ or cy5 fluorescently labelled PNA were synthesized by Eurogentec (Belgium) according to the following sequences.

Cyc-Bct;
(SEQ ID No: 10)
TGC CAT CAA GCT TAG AGG-$^{Cy5}$

Fluorescence Titrations

Fluorescence experiments were performed on a PTI spectrofluorimeter at 25° C. in a NaCl 154 mM buffer. Intrinsic Trp-fluorescence of VEPEP-5 was excited at 290 nm and emission spectrum was recorded between 310 and 400 nm, with a spectral band-pass of 2 and 8 nm for excitation and emission, respectively. FITC-fluorescence of labelled-peptide was excited at 492 nm and emission recorded between 500 and 580 nm. For VEPEP-3/peptide interaction, 0.5 µM of FITC-labelled peptide was titrated by increasing concentrations of VEPEP-5. All measurements were corrected for the dilution and curve fitting were performed by using Grafit software (Erithacus).

Characterization of Peptide-Based Nanoparticles

Mean particle size distribution was determined with a Coulter N4 Plus (Coulter-Beckman) at 25° C. for 3 min per measurement and zeta potential was measured with Zetasizer 4 apparatus (Malvern Ltd).

Cell Culture and VEPEP-Mediated Cargo Delivery

Adherent HS68 fibroblasts, HeLa, PC3, Jurkat, CEM-SS and U2OS MCF-7 cell lines (from American Type Culture Collection (ATCC)), as well as MEF and PBMC were cultured in Dulbecco's Modified Eagle's Medium supplemented with 2 mM glutamine, 1% antibiotics (streptomycin 10,000 µg/ml, penicillin, 10,000 IU/ml) and 10% (w/v) foetal calf serum (FCS), at 37° C. in a humidified atmosphere containing 5% $CO_2$. Stock solutions of VEPEP-5/peptide particles were prepared by complexing 1 µM peptide with VEPEP-5 peptides at a molar ratio of 1/20 for 30 min at 37° C. Lower concentrations of VEPEP-5-carrier/peptide (from 500 nM to 1 µM) were obtained by serial dilution of the stock complexes in PBS, in order to preserve the same VEPEP-5-carrier/peptide ratio. 150 000 cells seeded in a 35 mm dish the day prior transfection, were grown to 60% confluence and overlaid with 200 µl of preformed complexes, incubated for 3-5 min, then 400 µl of DMEM were added. After 30 min. incubation at 37° C., 1 ml of fresh DMEM containing 16% foetal calf serum (FCS) was added in order to reach a final FCS concentration of 10%, without removing the overlay of VEPEP-5/peptide complexes. Cells were returned to the incubator for 24 hrs. For CDK2 derived peptides cell proliferation was monitored after 24 and 48 hrs. Data reported are an average of 3 or 4 distinct experiments.

Cytotoxicity

Toxicity of VEPEP-5/peptide or VEPEP-5/SHM complexes was investigated on Hela and HS-68 cell lines. 30,000 cells seeded in 24-well plated the day prior transfection, were incubated with increasing concentrations of peptide or SHM complexed with VEPEP-5 at a 20/1 molar ratio ranging from 1 to 5 µM, for 30 min prior to addition of medium to reach a final 10% concentration of FCS. Cytotoxic response was measured 24 hr later by colorimetric MTT assay (Sigma, Germany), respectively. For MTT assay, cell culture medium was removed and replaced with PBS containing 2.5 mg/ml of MTT for 4 hr. Results correspond to the average of 3 separate experiments.

EXAMPLE 2

VEPEP-5 Peptides Form Stable Nanostructures with Different Cargoes

VEPEP-5 peptides (Short-6 (SEQ ID No: 1), Short-7 (SEQ ID No: 2) and Short 11 (SEQ ID No: 6)) form stable complexes with peptides, cyclic peptide, PNA and Protein. The binding of cargos was monitored by fluorescence spectroscopy using the both intrinsic Trp group of VEPEP-5 (3-4 Trp-residues) and extrinsic fluorescently labelled cargoes (using Cy5 or FITC). Curve fitting revealed that VEPEP-5 strongly binds the different cargoes with dissociation constant in the nanomolar range (Table 1 and FIG. 1).

TABLE 1

VEPEP-5/Cargo complexes characterization. Peptide (C4),
Cyclic peptide (PC4), PNA and protein (15 kDa).

| VEPEP-5 | Cargoes | | | |
|---|---|---|---|---|
| | peptide Kd (nM) | Cyc-pep Kd (nM) | PNA Kd (nM) | Protein Kd (nM) |
| Short 6 (SEQ ID No: 1) | 10-20 | 50-100 | 10-20 | 50-100 |
| Short 7 (SEQ ID No: 2) | 10-20 | 50-100 | 10-50 | 50-100 |
| Short 11 (SEQ ID No: 6) | 10-20 | 50-100 | 10-20 | 50-100 |

VEPEP-5 peptides also form stable particles with small aromatic molecules including doxorubicin, porphyrin and charges molecules including nucleotide, nucleoside and peptide-analog of nucleic acids or fluorescent dyes (FIG. 1). The dissociation constant for small hydrophobic molecule ranges between 0.05 to 0.1 µM, depending on the nature of the dyes and of the peptides (Table 2).

TABLE 2

VEPEP-5/Cargo complexes characterization. SHM: small
hydrophobic molecules (porphyrin, FAM-G, doxorubicin)

| VEPEP-5 | Cargoes | | | | | |
|---|---|---|---|---|---|---|
| | Doxorubicin | | porphyrin | | FAM-guanosine | |
| | Binding | Kd (µM) | Binding | Kd (µM) | Binding | Kd (µM) |
| Short 6 | yes | 0.05 | yes | 0.4 | yes | 0.06 |
| Short 7 | yes | 0.07 | yes | 0.5 | yes | 0.05 |
| Short 11 | yes | 0.1 | yes | 0.7 | yes | 0.1 |

Figure 2:
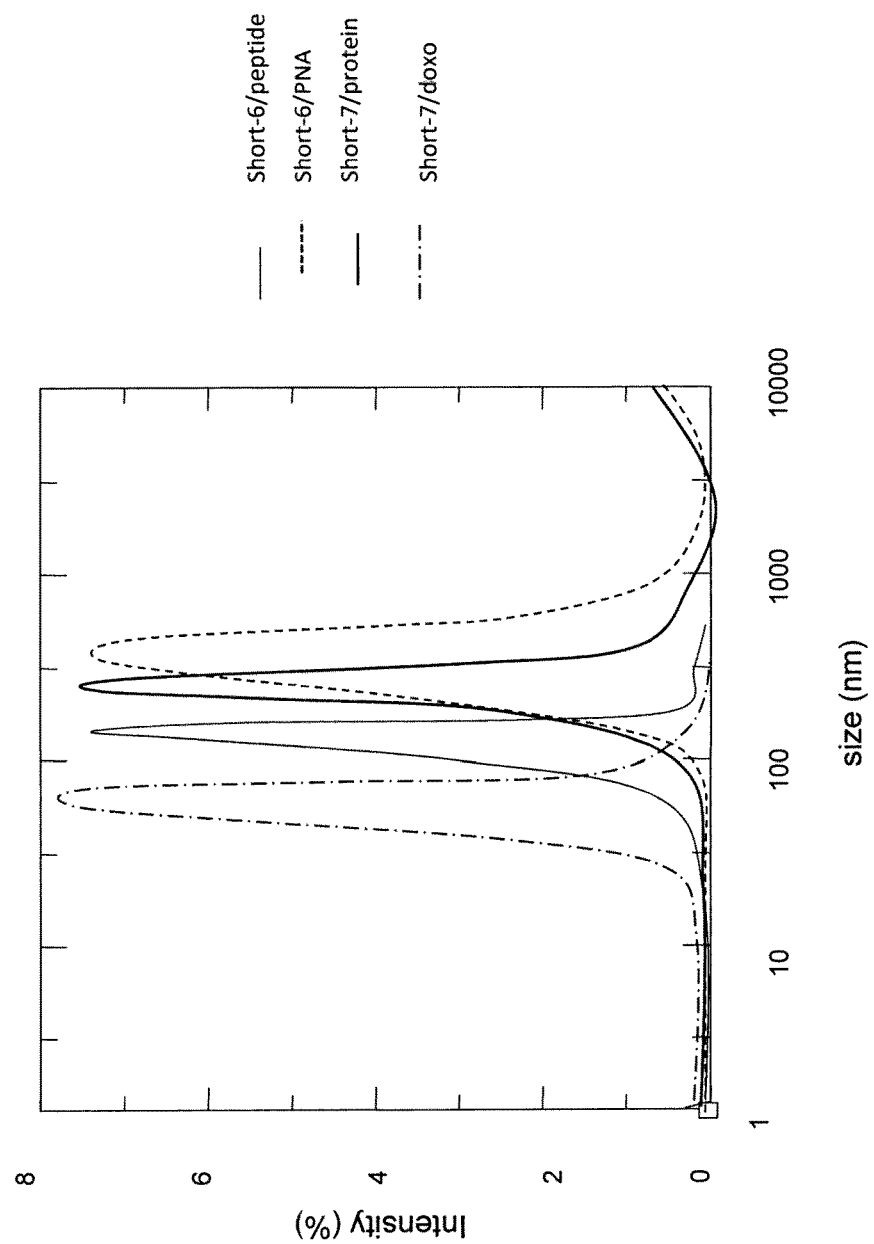

The size of the particles was monitored by dynamic light scattering. The optimal VEPEP-5 peptide/cargo (peptide and SHM) molar ratio is ranging between 1/10 to 1/30 (FIG. 2). The size of the particles is of about 50 to 200 nanometer in diameter.

EXAMPLE 3

VEPEP-5 Mediated Delivery of Peptide and Cyclic Peptide in Different Cell Lines VEPEP-5 peptides (Short-6, Short-7 and Short 11) have been used for the delivery of different peptides into different cell lines, including primary cell lines, stem cell lines and challenging cell lines. Peptide delivery was monitored using three approaches, fluorescence spectroscopy and monitoring biological responses (anti proliferation)

1—Fluorescent labelled peptide was visualized in the different cell lines using fluorescence microscopy or FACS sorting (Table 3). In most of the cell lines, the uptake of Cy-5 labelled peptides is more than 70% of the cells 2—Dose-response experiments performed on different cultured cells revealed that VEPEP-5-mediated delivery of C4 peptides, targeting cdk2/cyclin A complex blocks cell proliferation of different cancer cells (FIG. 3).

TABLE 3

| Cell lines | origin | Short 6 Efficiency | Short 7 Efficiency | Short 11 Efficiency |
|---|---|---|---|---|
| Hela | Human epithelial cervical cells | 45% | 70% | 69% |
| MEF | Mouse fibroblast | 64% | 71% | 70% |
| HS-68 | Human fibroblast | 89% | 78% | 80% |
| CEM-SS | Human macrophage | 74% | 75% | 70% |
| U2OS | Human osteoblast | 68% | 71% | 55% |
| MCF7 | Human breast adenocarcinoma | 59% | 75% | 58% |
| PBMC | Human macrophage | 78% | 80% | 78% |

Figure 3:
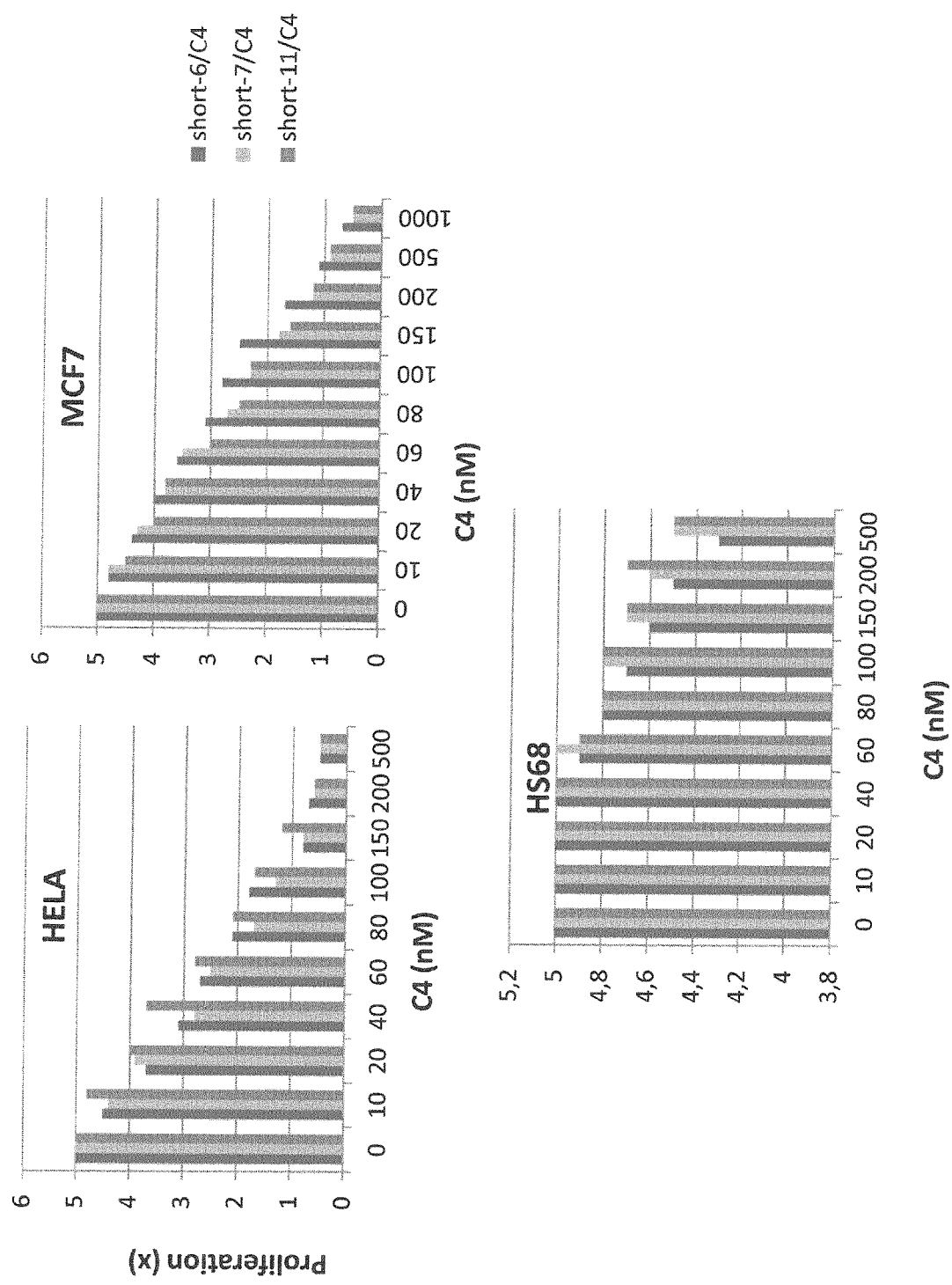

VEPEP5-Mediated Delivery of Peptide Targeting Cdk2/Cyclin A Blocks Cancer Cell Proliferation Dose-response experiments performed on cultured cells revealed that VEPEP-5 (Short-6, Short-7 and Short 11) mediated delivery of C4 peptide induced a robust biological response associated with specific cell cycle arrest (FIG. 3). A peptide C4 concentration of 100 nM was sufficient to block proliferation of Hela and MCF7 cells. Using Short6 peptide an $IC_{50}$ of 80±20 nM and 50±10 nM were estimated for C4 peptides respectively on Hela and MCF7. Using short7 peptide an $IC_{50}$ of 45±10 nM and 80±20 nM were estimated for C4 peptides respectively on Hela and MCF7. Using short11 peptide an $IC_{50}$ of 150±30 nM and 200±20 nM were estimated for C4 peptides respectively on Hela and MCF7. In contrast, proliferation was only reduced by 10 to 20 for non-transformed HS68 fibroblasts (FIG. 3) in perfect agreement with the impact of the check point G2-M on the cell cycle proliferation and showing the specificity of the peptide for cancer cells.

VEPEP-5 Mediated Delivery of PNA Molecule in Different Cell Lines

Figure 4:
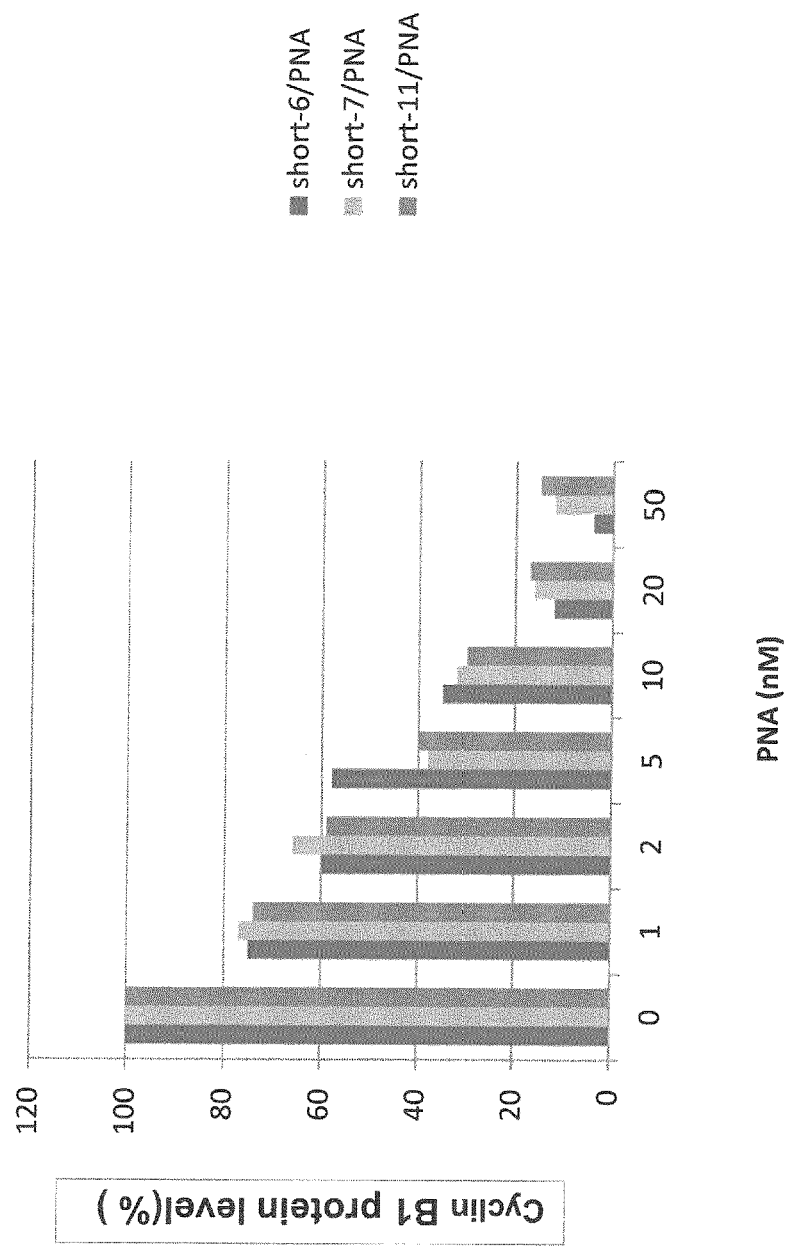

VEPEP-5 (Short-6, Short-7 and Short 11) peptides have been used for the delivery of nucleic acid analog (PNA and morpholino) into different cell lines, including primary cell lines and challenging cell lines. Uptake was monitored by following biological response (Cyclin B1 knockdown). We then have applied Short-6, Short-7 and Short 11 for the delivery of PNA antisense targeting Cyclin B1 as previously described by Morris et al. [13]. Dose-response experiments performed on different cultured cells revealed that VEPEP-9-mediated delivery of PNA (Cyclin B1) induced a robust downregulation higher than 70% of Cyclin B1 protein level in Hela and MCF7 cells and no change in Cyclin 131 level was observed with free PNA and scrambled PNA molecule complexed with Short-6 and Short-11 carrier (FIG. 4).

Figure 5:
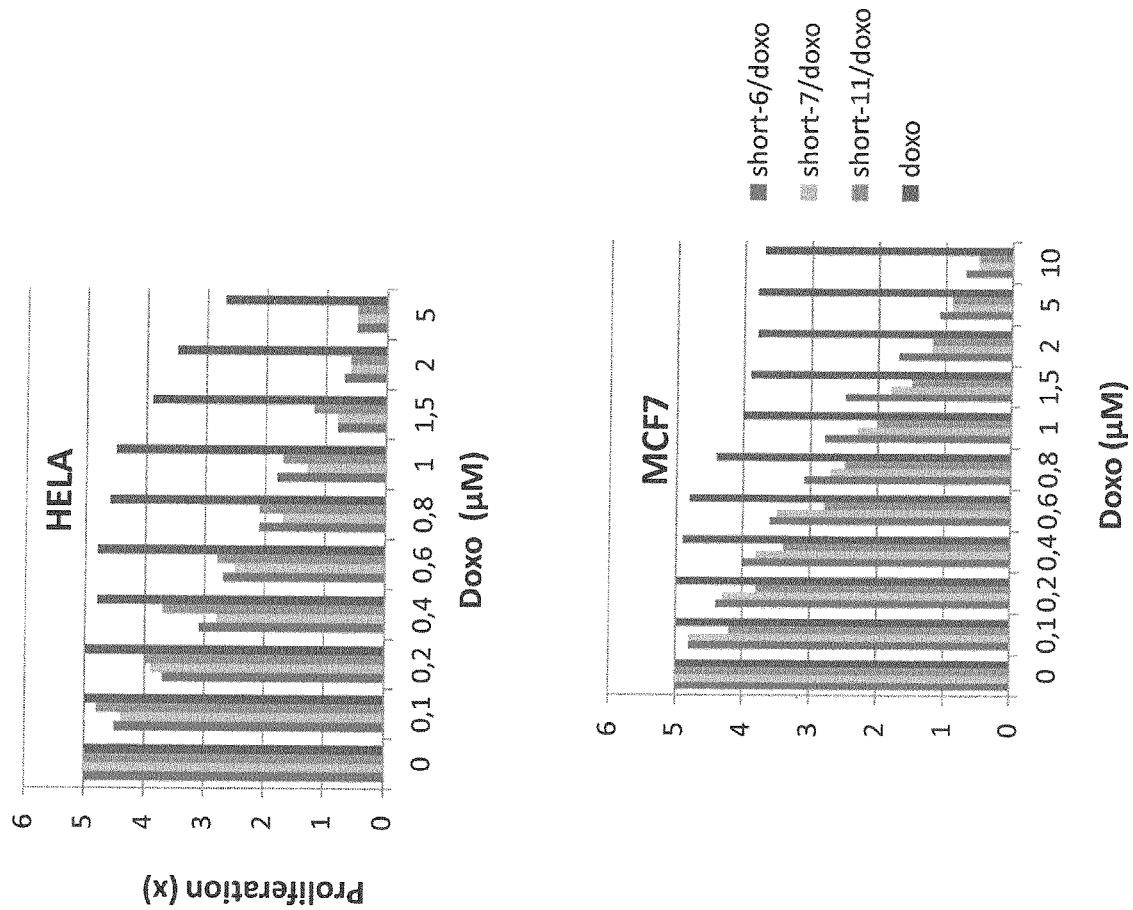

VEPEP-5 Mediated Delivery of Small Hydrophobic Molecules in Different Cell Lines VEPEP-5 peptides (Short-6, Short-7 and Short 11) have been used for the delivery of different small hydrophobic molecules including doxorubicin and porphyrin on different cell lines including primary cell lines and challenging cell lines. VEPEP-5 peptides form stable particles with small aromatic molecules (table 2). Effect of VEPEP-5 mediated delivery of doxorubicin and porphyrin have been investigated on cancer cell viability. Dose-response experiments performed on cultured cells revealed that VEPEP-5 mediated delivery of doxorubicin and porphyrin induced a biological response associated to cell cycle arrest and decrease in viability of MCF7, Hela cancer cells (FIG. 5). The impact of carrier peptides to improve cellular uptake of small molecule drugs was estimated by following inhibition of proliferation of cancer cells. $IC_{50}$ are reported in Table 4. Comparison of VEPEP-5 mediated drug delivery with the response obtained with free drug, demonstrated that Doxo and porphyrin are between 25 to 50-fold more efficient when associated to VEPEP-5.

TABLE 4

| Drug | Short 6 IC50 (μM) | Short 7 IC50 (μM) | Short 11 IC50 (μM) | Free drug IC50 (μM) |
|---|---|---|---|---|
| Doxo (Hela) | 0.3 | 0.5 | 0.7 | 10 |
| Doxo (MCF7) | 0.5 | 0.7 | 0.2 | 9 |
| Porphyrin (Hela) | 0.7 | 0.5 | 0.5 | 25 |
| Porphyrin (MCF7) | 0.5 | 0.9 | 1.5 | 17 |

VEPEP-5 Mediated Delivery of Proteins in Different Cell Lines

VEPEP-5 have been used for the delivery of different proteins into different cell lines, including primary cell lines, stem cell lines and challenging cell lines. Protein uptake was monitored using fluorescence spectroscopy and FACS analysis. GFP/RFP or Fluorescent labelled proteins were visualized in the different cell lines using fluorescence microscopy or FACS sorting (Table 5). In most of the cell lines, the uptake of RFP; GFP, Cy-5 labelled proteins is more than 50% of the cells.

TABLE 5

| Cell lines | origin | Short 6 | Short 7 | Short 11 |
|---|---|---|---|---|
| Hela | Human epithelial cervical cancer cells | 55% | 80% | 60% |
| Jurkat | Human T lymphocyte | 60% | 70% | 78% |
| MEF | Mouse fibroblast | 65% | 65% | 60% |
| HS-68 | Human fibroblast | 78% | 80% | 70% |
| CEM-SS | Human macrophage | 55% | 60% | 65% |
| U2OS | Human osteoblast | 64% | 80% | 71% |
| MCF7 | Human breast adenocarcinoma | 70% | 75% | 62% |

EXAMPLE 4

VEPEP5-Mediated Delivery of Peptide/PNA and SHM is not Toxic

Figure 6:
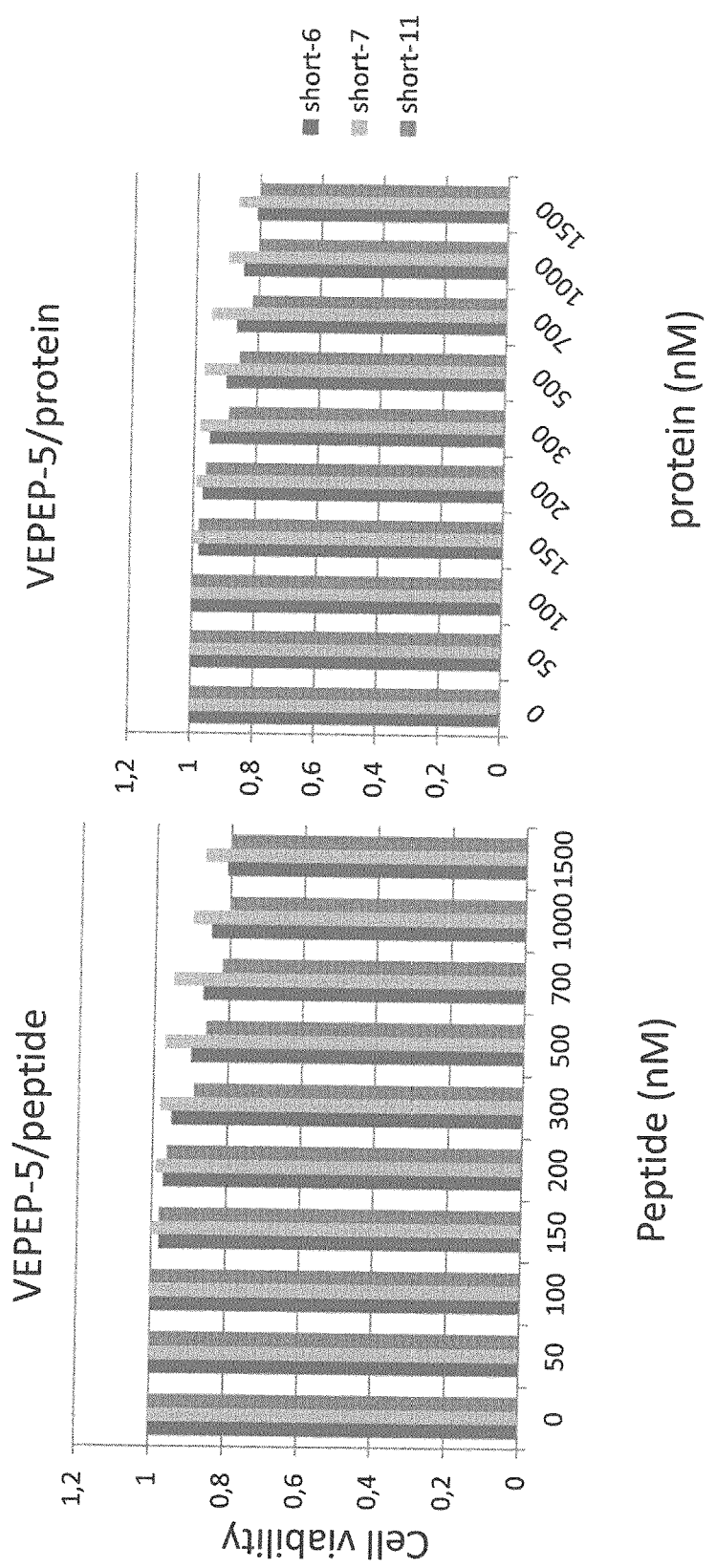

As shown on FIG. 6, the toxicity of VEPEP-5 (Short-6, Short-7, Short-11) particles was investigated on HeLa and U2OS cells by MTT assay. No toxicity was detected at levels up to 200 nM, and only a mild toxicity was observed at the maximum concentration of 1 μM.

REFERENCES

[1] D J. Glover, H J. Lipps, D A. Jans, Towards safe, non-viral therapeutic gene expression in humans. Nat. Rev. Genet. 6 (2005) 299-310

[2] K A. Whitehead, R. Langer, D G. Anderson, Knocking down barriers: advances in siRNA delivery. Nat Rev Drug Discov. 8 (2009) 129-138.

[3] Ü Langel, Handbook of Cell-Penetrating Peptides: (Eds.: U. Langel) CRC Taylor & Francis, Boca Raton (2007).

[4] F. Heitz, M C. Morris, G. Divita, Twenty years of cell-penetrating peptides: from molecular mechanisms to therapeutics; British Journal of Pharmacology 157 (2009) 195-206.

[5] S. Deshayes, M C Morris, F. Heitz, G. Divita. Delivery of proteins and nucleic acids using a non-covalent peptide-based strategy. Adv Drug Deliv Rev. 60 (2008) 537-547.

[6] S. Deshayes, M. C. Morris, G. Divita, F. Heitz Cell-penetrating peptides: tools for intracellular delivery of therapeutics, Cell Mol Life Sci. 62 (2005) 1839-1849.

[7] M C. Morris, P. Vidal, L. Chaloin, F. Heitz, G Divita A new peptide vector for efficient delivery of oligonucleotides into mammalian cells, Nucleic Acids Res. 25 (1997) 2730-2736.

[8] M C. Morris, J. Depollier, J. Mery, F. Heitz, G. Divita A peptide carrier for the delivery of biologically active proteins into mammalian cells, Nat. Biotechnol. 19 (2001) 1173-1176.

[9] Mery J, Brugidou J, Derancourt J. Disulfide bond as peptide-resin linkage in Boc-Bzl SAPS, for potential biochemical applications, Pept Res. 1992 July-August; 5(4): 233-40.

[10] L. Crombez, M. C. Morris, S. Dufort, G. Aldrian-Herrada, Q. Nguyen, G. Mc Master, J. L. Coll, F. Heitz, G. Divita, Targeting cyclin B1 through peptide-based delivery of siRNA prevents tumour growth, Nucleic Acids Res. 37 (2009) 4559-4569.

[11] L. Crombez, G. Aldrian-Herrada, K, Konate, Q. N. Nguyen, G. K. McMaster, R. Brasseur, F. Heitz, G. Divita, A new potent secondary amphipathic cell-penetrating peptide for siRNA delivery into mammalian cells, Mol. Ther. 17 (2009) 95-103.

[12] Verdine, G. L. and Hilinski, G. J. (2012), Stapled peptides for intracellular chug targets. Methods in Enzymology, vol 503, p 3-33.

[13] Morris M C, Gros E, Aldrian-Herrada G, Choob M, Archdeacon J,
Heitz F, Divita G. A non-covalent peptide-based earner for in vivo delivery of DNA mimics. *Nucleic Acids Res.* 2007; 35(7):e49.

The invention claimed is:

1. A 10 amino acid cell-penetrating peptide characterized in that it comprises an amino acid sequence consisting of a beta-alanine or a serine in the N-terminal position, linked to a sequence consisting of 9 consecutive amino acids from the sequence

RXWXRLWXRLR, (SEQ ID NO: 7)

wherein X in position 2 is R or S and X in positions 4 and 8 are, independently from each other, W or F.

2. The cell-penetrating peptide of claim 1, wherein the amino acid sequence is selected from the group consisting of:

$X_1$WWRLWWRLR, (SEQ ID No: 1)

$X_1$WFRLWFRLR, (SEQ ID No: 2)

(SEQ ID No: 3)

-continued

X₁WFRLWWRLR, (SEQ ID No: 4)
X₁WWRLWFRLR, (SEQ ID No: 5)
X₁RWWRLWWRL,
and (SEQ ID No: 6)
X₁RSWFRLWFR, wherein X₁ is beta-A or S.

3. The cell-penetrating peptide of claim 1, further comprising, covalently linked to the N-terminal end of the amino acid sequence, one or several chemical entities selected from the group consisting of an acetyl, a fatty acid, a cholesterol, a poly-ethylene glycol, a nuclear localization signal, a nuclear export signal, an antibody, a polysaccharide and a targeting molecule.

4. The cell-penetrating peptide of claim 1, further comprising, covalently linked to the C-terminal end of said amino acid sequence, one or several groups selected from the group consisting of a cysteamide, a cysteine, a thiol, an amide, an optionally substituted nitrilotriacetic acid, a carboxyl, a linear or branched optionally substituted $C_1$-$C_6$ alkyl, a primary or secondary amine, an osidic derivative, a lipid, a phospholipid a fatty acid, a cholesterol, a poly-ethylene glycol, a nuclear localization signal, a nuclear export signal, an antibody, a polysaccharide and a targeting molecule.

5. A complex comprising a cell-penetrating peptide according to claim 1 and a cargo selected from the group consisting of proteins, nanobodies, peptides, peptide-analogues, uncharged oligonucleotides, PNAs and small hydrophobic molecules.

6. The complex of claim 5, wherein said cargo is a molecule of at most 1.5 kDa.

7. The complex of claim 5, wherein said cargo is an anticancer or an anti viral drug.

8. The complex of claim 5, wherein said cargo is selected from the group consisting of amino acids, di- or tri- peptides, daunomycin, Paclitaxel, doxorubicin, AZT, porphyrin, fluorescently labelled nucleosides or nucleotides, hydrophobic maghemite and fluorescent dyes.

9. The complex of claim 5, wherein said cargo is a cosmetic agent.

10. The complex of claim 5, wherein the size of the complex is between 50 and 200 nm.

11. A nanoparticle comprising a complex according to claim 5, coated by a layer of peripheral cell-penetrating peptides, wherein said peripheral cell-penetrating peptides have a peptide sequence different from SEQ ID Nos: 1 to 6.

12. A nanoparticle comprising a core which comprises a cargo complexed to a first entity selected from the group consisting of cell-penetrating peptides, liposomes, polycationic structures and carbon nanoparticles, wherein said core is coated by peripheral cell-penetrating peptides, and wherein the peripheral cell-penetrating peptides have the peptide sequence of a cell-penetrating peptide according to claim 1.

13. The nanoparticle of claim 12, wherein said first entity is a cell-penetrating peptide selected from the group consisting of VEPEP-3, VEPEP-6, VEPEP-9, CADY, MPG, PEP-1, PPTG1, and poly Arginine.

14. The nanoparticle of claim 12, wherein the size of the nanoparticle is between 20 and 300 nm.

15. The nanoparticle of claim 12, wherein the peripheral cell-penetrating peptides comprise a poly-ethylene glycol group covalently linked to their N-terminus, and/or a cysteamide group covalently linked to their C-terminus.

16. The nanoparticle of claim 12, wherein at least some of the peripheral cell-penetrating peptides are bound to a targeting molecule.

17. The nanoparticle of claim 12, for use as a medicament.

18. The nanoparticle of claim 12, for use as a marker or an imaging agent.

19. A therapeutic, cosmetic or diagnostic composition comprising a nanoparticle according to claim 12.

20. The composition of claim 19, which is formulated for intravenous, intratumoral, topical, intrarectal, intranasal, transdermal, or intradermal administration, or for administration via a mouth spray, or for administration as a subcutaneous implant for slow release of a drug.

21. A method for delivering a molecule into a cell in vitro, comprising a step of putting said cell into contact with a nanoparticle according to claim 12, wherein the cargo of the nanoparticle is said molecule.

* * * * *